(12) United States Patent
Kanno et al.

(10) Patent No.: US 9,272,980 B2
(45) Date of Patent: Mar. 1, 2016

(54) ANTICANCER AGENT

(71) Applicant: KTN BioTec, Inc., Hirakata-shi, Osaka (JP)

(72) Inventors: Takeshi Kanno, Nishinomiya (JP); Akito Tanaka, Toyonaka (JP); Tadashi Shimizu, Kobe (JP); Takashi Nakano, Kobe (JP); Tomoyuki Nishizaki, Kobe (JP)

(73) Assignee: KTN BioTec, Inc., Osaka (JP)

( * ) Notice: Subject to any disclaimer, the term of this patent is extended or adjusted under 35 U.S.C. 154(b) by 0 days.

(21) Appl. No.: 14/298,400

(22) Filed: Jun. 6, 2014

(65) Prior Publication Data
US 2015/0353473 A1  Dec. 10, 2015

(51) Int. Cl.
*A61K 31/497* (2006.01)
*C07C 217/94* (2006.01)
*C07C 217/78* (2006.01)
*C07C 217/80* (2006.01)
*C07C 217/54* (2006.01)

(52) U.S. Cl.
CPC ............. *C07C 217/94* (2013.01); *C07C 217/54* (2013.01); *C07C 217/78* (2013.01); *C07C 217/80* (2013.01)

(58) Field of Classification Search
USPC ...................................... 585/454; 514/252.12
See application file for complete search history.

(56) References Cited

U.S. PATENT DOCUMENTS 3,997,666 A     12/1976 Witte et al.
6,673,802 B2 *   1/2004 Castelhano et al. ....... 514/263.2

FOREIGN PATENT DOCUMENTS

JP    1975-121286 A    9/1975

OTHER PUBLICATIONS

Kano et al., Pharmacology, 91:339-345, 2013.*
Suzuki et al. CAS: 127: 259, 1997.*
Triggle et al. CAS: 105: 97329, 1986.*
Towler et al. CAS: 149: 518754, 2008.*
Seki et al. CAS: 126: 42259, 1996.*
Yasuda et al. CAS: 109: 6533,1998.*
Quin et al. CAS: 38: 5019, 1944.*
Brede et al., *Biol. Cell*, 96: 343-348 (2004).
Gotoh et al., *Pharmacology*, 90: 242-246 (2012).
Hori et al., *Cancer Prev. Res.*, 4(1): 87-96 (2011).
Kanda et al., *Int. J. Cancer*, 122: 444-451 (2008).
Kanno et al., *Pharmacology*, 91: 339-345 (2013).
Kaumann et al., *Naunyn-Schmiedeberg's Arch Pharmacol.*, 355: 667-681 (1997).
Takei et al., *Jpn. J. Pharmacol.*, 79: 447-454 (1999).
Zhong et al., *Eur. J. Pharmacol.*, 375: 261-276 (1999).

* cited by examiner

*Primary Examiner* — Rei-Tsang Shiao
(74) *Attorney, Agent, or Firm* — Leydig, Voit & Mayer, Ltd.

(57) ABSTRACT

The present invention aims to provide a compound having an anticancer action comparable or superior to that of naftopidil. A compound represented by the formula (I)

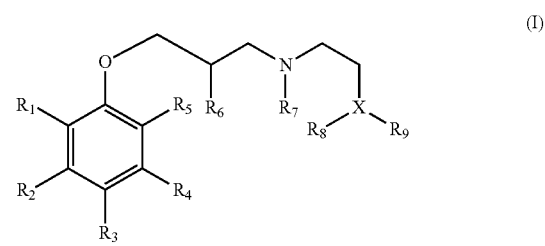

wherein each symbol is as defined in the SPECIFICATION, or a pharmaceutically acceptable salt thereof, particularly 1-((2-((2-methoxyphenyl)amino)ethyl)amino)-3-(1-naphthyloxy)propan-2-ol, or a pharmaceutically acceptable salt thereof. The compound shows a cell proliferation suppressive action on a wide range of cancer cells, is useful as an anticancer agent, and is useful for the prophylaxis and/or treatment of cancer.

16 Claims, 4 Drawing Sheets

ANTICANCER AGENT

TECHNICAL FIELD OF THE INVENTION

The present invention relates to an aryloxy derivative and use thereof. More particularly, the present invention relates to an anti-cancer agent containing an aryloxy derivative as an active ingredient.

BACKGROUND OF THE INVENTION

Naftopidil is an $\alpha_1$ adrenoceptor antagonist having high selectivity to $\alpha_{1A}$-/$\alpha_{1D}$ receptor, and is clinically used as a therapeutic drug for prostatomegaly and hypertension (Takei R, et al., Jpn J Pharmacol 1999; 79:447-454). The chemical name of naftopidil is (($\pm$)-1-[4-(2-methoxyphenyl)piperazinyl]-3-(1-naphthyloxy)propan-2-ol, which is a substance represented by the following formula and created by Boehringer•Mannheim (now Roche) in Germany

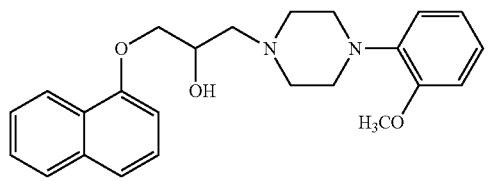 [SMILES: COc1ccccc1N1CCN(CC(O)COc2cccc3ccccc23)CC1]

It was first disclosed in JP-A-50-121286 together with a pharmaceutically acceptable salt thereof. In recent years, it has been reported that naftopidil also has an anticancer action. For example, naftopidil was shown to inhibit the growth of prostate cancer cell by discontinuing the G1 phase of the cell cycle (Hori Y, et al., Cancer Prev Res (Phila) 2011; 4:87-96; Kanda H, et al., Int J Cancer 2008; 122:444-451).

In an earlier study, the present inventors reported that naftopidil decreases the cell survival rate of the cell lines of bladder cancer, prostate cancer and kidney cancer (Gotoh A, et al., "Anti-tumor action of α1-adrenoceptor blockers on human bladder, prostate, and kidney cancer cells." Pharmacology 2012; 90:242-246). Naftopidil also induces apoptosis in the cell line of malignant mesothelioma. From these findings, the possibility of naftopidil being promising as an anticancer agent is considered. However, the mechanism of the anticancer action of naftopidil contains aspects yet to be clarified.

$\alpha_1$-adrenoceptor is divided into 3 subtypes of $\alpha_{1A}$-, $\alpha_{1B}$- and $\alpha_{1D}$-. They conjugate with $G_{q/11}$ protein, activate phospholipase C and then activate protein kinase C (PKC) (Brede M, et al., Biol Cell 2004; 96:343-348; Kaumann A J, and Molenaar P, Naunyn Schmiedebergs Arch Pharmacol 1997; 355:667-681; Zhong H, and Minneman K P, Eur J Pharmacol 1999; 375:261-276). Accordingly, naftopidil inhibits PKC by inhibiting $\alpha_1$-adrenoceptor. However, GF109203X, which is a PKC inhibitor, does not potentiate apoptosis of malignant mesothelioma induced by naftopidil, but conversely weakened the effect of naftopidil (data not shown). Furthermore, the growth of malignant mesothelioma cells was promoted by knocking-down $\alpha_{1D}$-adrenoceptor (data not shown). These results suggest that naftopidil induces apoptosis of malignant mesothelioma cells by a mechanism different from the inhibition of $\alpha_1$-adrenoceptor. As the situation stands, however, the mechanism thereof has not been elucidated yet.

DISCLOSURE OF THE INVENTION

The present invention aims to provide a compound having an anticancer action comparable or superior to that of naftopidil.

In view of the above-mentioned problem, the present inventors have synthesized various derivatives of naftopidil, and selected a series of aryloxy derivatives capable of exhibiting a superior anticancer action, which resulted in the completion of the present invention.

Accordingly, the present invention is as follows.

[1] A method for the prophylaxis or treatment of cancer, comprising administering an effective amount of a compound represented by the formula (I)

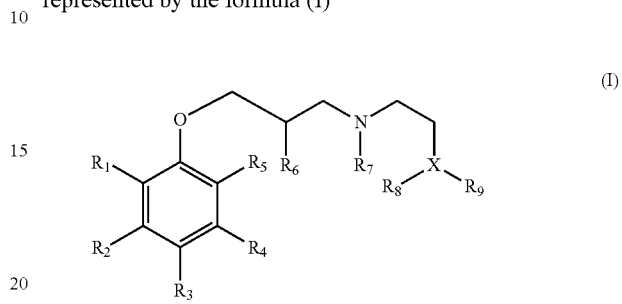

wherein
$R^1$-$R^5$ are the same or different and each is a hydrogen atom, a halogen atom, or a $C_{2-6}$ alkenyl group;
$R^1$ and $R^2$, or $R^2$ and $R^3$ optionally form a benzene ring together with a carbon atom bonded thereto;
$R^6$ is a hydrogen atom, a hydroxyl group or a $C_{1-6}$ alkoxy group;
$R^7$ and $R^8$ are the same or different and each is a hydrogen atom or a $C_{1-6}$ alkyl group;
$R^7$ and $R^8$ optionally form a ring together with a nitrogen atom bonded thereto and X;
X is CH or N;
$R^9$ is an optionally substituted $C_{6-10}$ aryl group or an optionally substituted $C_{1-10}$ alkyl group,
(provided when $R^1$ and $R^2$ form a benzene ring together with a carbon atom bonded thereto, $R^7$ and $R^8$ form a ring together with a nitrogen atom bonded thereto and X, and $R^6$ is a hydroxyl group, then $R^9$ is not a phenyl group substituted by a methoxy group) or a pharmaceutically acceptable salt thereof to a patient in need thereof.

[2] The method of the above-mentioned [1], wherein the compound represented by the formula (I) is
3-(1-naphthyloxy)-1-(4-phenylpiperazinyl)propan-2-ol (HUHS1004),
1-(4-(2-methoxyphenyl)piperazinyl)-3-phenoxypropan-2-ol (HUHS1006),
1-(4-(2-methoxyphenyl)piperazinyl)-3-(2,3,4,6-tetrachlorophenoxyl)propan-2-ol (HUHS1007),
1-(4-methylpiperazinyl)-3-(1-naphthyloxy)propan-2-ol (HUHS1008),
1-(4-isopropylpiperazinyl)-3-(1-naphthyloxy)propan-2-ol (HUHS1009),
3-(1-naphthyloxy)-1-(4-propylpiperazinyl) propan-2-ol (HUHS1010),
1-(4-diphenylmethylpiperazinyl)-3-(1-naphthyloxy)-propan-2-ol (HUHS1011),
3-(1-naphthyloxy)-1-(4-(phenylcarbonyl)piperazinyl)propan-2-ol (HUHS1012),
3-(1-naphthyloxy)-1-(4-(2-methoxyphenyl)piperazinyl)-2-propylmethylether (HUHS1013),
1-(4-(2-chlorophenyl)piperazinyl)-3-(1-naphthyloxy)-propan-2-ol (HUHS1014),
1-((2-((2-methoxyphenyl)amino)ethyl)amino)-3-(1-naphthyloxyl)propan-2-ol (HUHS1015), 1-(2-methoxyphenyl)-4-(3-(1-naphthyloxyl)propyl)piperazine (HUHS1016),
1-(4-(2-methoxyphenyl)piperidin-1-yl)-3-(1-naphthyloxyl)propan-2-ol (HUHS1017),
1-(4-heptylpiperazinyl)-3-(1-naphthyloxy) propan-2-ol (HUHS1018),
3-(1-naphthyloxy)-1-(4-octylpiperazinyl)propan-2-ol (HUHS1019),
3-(1-naphthyloxy)-1-(4-(1-naphthyl)piperazinyl)propan-2-ol (HUHS1020) or
3-(1-naphthyloxy)-1-(4-(2-naphthyl)piperazinyl)propan-2-ol (HUHS1021).

[3] The method of the above-mentioned [1], wherein the compound represented by the formula (I) is
3-(1-naphthyloxy)-1-(4-phenylpiperazinyl)propan-2-ol (HUHS1004),
1-(4-(2-methoxyphenyl)piperazinyl)-3-phenoxypropan-2-ol (HUHS1006),
1-(4-(2-methoxyphenyl)piperazinyl)-3-(2,3,4,6-tetrachlorophenoxyl)propan-2-ol (HUHS1007),
1-(4-diphenylmethylpiperazinyl)-3-(1-naphthyloxy)-propan-2-ol (HUHS1011),
3-(1-naphthyloxy)-1-(4-(phenylcarbonyl) piperazinyl) propan-2-ol (HUHS1012),
3-(1-naphthyloxy)-1-(4-(2-methoxyphenyl)piperazinyl)-2-propylmethylether (HUHS1013),
1-(4-(2-chlorophenyl)piperazinyl)-3-(1-naphthyloxy)-propan-2-ol (HUHS1014),
1-((2-((2-methoxyphenyl)amino)ethyl)amino)-3-(1-naphthyloxyl)propan-2-ol (HUHS1015),
1-(2-methoxyphenyl)-4-(3-(1-naphthyloxy)propyl)piperazine (HUHS1016),
1-(4-(2-methoxyphenyl) piperidin-1-yl)-3-(1-naphthyloxy) propan-2-ol (HUHS1017),
1-(4-heptylpiperazinyl)-3-(1-naphthyloxyl)propan-2-ol (HUHS1018),
3-(1-naphthyloxy)-1-(4-octylpiperazinyl)propan-2-ol (HUHS1019),
3-(1-naphthyloxy)-1-(4-(1-naphthyl)piperazinyl)propan-2-ol (HUHS1020) or
3-(1-naphthyloxy)-1-(4-(2-naphthyl)piperazinyl)propan-2-ol (HUHS1021).

[4] The method of the above-mentioned [1], wherein the compound represented by the formula (I) is
3-(1-naphthyloxy)-1-(4-phenylpiperazinyl)propan-2-ol (HUHS1004),
1-(4-(2-methoxyphenyl)piperazinyl)-3-phenoxypropan-2-ol (HUHS1006),
1-(4-diphenylmethylpiperazinyl)-3-(1-naphthyloxy)-propan-2-ol (HUHS1011),
1-(4-(2-chlorophenyl)piperazinyl)-3-(1-naphthyloxy)-propan-2-ol (HUHS1014),
1-((2-((2-methoxyphenyl)amino)ethyl)amino)-3-(1-naphthyloxyl)propan-2-ol (HUHS1015),
1-(4-(2-methoxyphenyl)piperidin-1-yl)-3-(1-naphthyloxy) propan-2-ol (HUHS1017),
1-(4-heptylpiperazinyl)-3-(1-naphthyloxyl)propan-2-ol (HUHS1018) or
3-(1-naphthyloxy)-1-(4-octylpiperazinyl)propan-2-ol (HUHS1019).

[5] The method of the above-mentioned [1], wherein the compound represented by the formula (I) is 1-((2-((2-methoxyphenyl)amino)ethyl)amino)-3-(1-naphthyloxyl)propan-2-ol (HUHS1015).

[6] The method of any of the above-mentioned [1]-[5], wherein the cancer is at least one kind selected from the group consisting of mesothelioma, lung cancer, liver cancer, gastric cancer and bladder cancer.

[7] A compound represented by the formula (I)

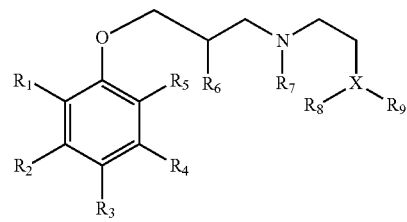

wherein
$R^1$-$R^5$ are the same or different and each is a hydrogen atom, a halogen atom or a $C_{2-6}$ alkenyl group;
$R^1$ and $R^2$, or $R^2$ and $R^3$ optionally form a benzene ring together with a carbon atom bonded thereto;
$R^6$ is a hydrogen atom, a hydroxyl group or a $C_{1-6}$ alkoxy group;
$R^7$ and $R^8$ are the same or different and each is a hydrogen atom or a $C_{1-6}$ alkyl group;
$R^7$ and $R^8$ optionally form a ring together with a nitrogen atom bonded thereto and X;
X is CH or N;
$R^9$ is an optionally substituted $C_{6-10}$ aryl group or an optionally substituted $C_{1-10}$ alkyl group,
(provided when $R^1$ and $R^2$ form a benzene ring together with a carbon atom bonded thereto, $R^7$ and $R^8$ form a ring together with a nitrogen atom bonded thereto and X, and $R^6$ is a hydroxyl group, then $R^9$ is not a phenyl group substituted by a methoxy group) or a pharmaceutically acceptable salt thereof.

[8] The compound of the above-mentioned [7], wherein the compound represented by the formula (I) is
3-(1-naphthyloxy)-1-(4-phenylpiperazinyl)propan-2-ol (HUHS1004),
1-(4-(2-methoxyphenyl)piperazinyl)-3-phenoxypropan-2-ol (HUHS1006),
1-(4-(2-methoxyphenyl)piperazinyl)-3-(2,3,4,6-tetrachlorophenoxyl)propan-2-ol (HUHS1007),
1-(4-methylpiperazinyl)-3-(1-naphthyloxy)propan-2-ol (HUHS1008),
1-(4-isopropylpiperazinyl)-3-(1-naphthyloxy)propan-2-ol (HUHS1009),
3-(1-naphthyloxy)-1-(4-propylpiperazinyl)propan-2-ol (HUHS1010),
1-(4-diphenylmethylpiperazinyl)-3-(1-naphthyloxy)-propan-2-ol (HUHS1011),
3-(1-naphthyloxy)-1-(4-(phenylcarbonyl)piperazinyl)propan-2-ol (HUHS1012),
3-(1-naphthyloxy)-1-(4-(2-methoxyphenyl)piperazinyl)-2-propylmethylether (HUHS1013),
1-(4-(2-chlorophenyl) piperazinyl)-3-(1-naphthyloxy)-propan-2-ol (HUHS1014),
1-((2-((2-methoxyphenyl)amino)ethyl)amino)-3-(1-naphthyloxyl)propan-2-ol (HUHS1015),
1-(2-methoxyphenyl)-4-(3-(1-naphthyloxyl)propyl)piperazine (HUHS1016),
1-(4-(2-methoxyphenyl)piperidin-1-yl)-3-(1-naphthyloxyl) propan-2-ol (HUHS1017), 1-(4-heptylpiperazinyl)-3-(1-naphthyloxyl)propan-2-ol (HUHS1018),
3-(1-naphthyloxy)-1-(4-octylpiperazinyl)propan-2-ol (HUHS1019),
3-(1-naphthyloxy)-1-(4-(1-naphthyl)piperazinyl)propan-2-ol (HUHS1020) or
3-(1-naphthyloxy)-1-(4-(2-naphthyl)piperazinyl)propan-2-ol (HUHS1021), or a pharmaceutically acceptable salt thereof.

[9] The compound of the above-mentioned [7], wherein the compound represented by the formula (I) is
3-(1-naphthyloxy)-1-(4-phenylpiperazinyl)propan-2-ol (HUHS1004),
1-(4-(2-methoxyphenyl)piperazinyl)-3-phenoxypropan-2-ol (HUHS1006),
1-(4-(2-methoxyphenyl)piperazinyl)-3-(2,3,4,6-tetrachlorophenoxyl)propan-2-ol (HUHS1007),
1-(4-diphenylmethylpiperazinyl)-3-(1-naphthyloxy)-propan-2-ol (HUHS1011),
3-(1-naphthyloxy)-1-(4-(phenylcarbonyl)piperazinyl)propan-2-ol (HUHS1012),
3-(1-naphthyloxy)-1-(4-(2-methoxyphenyl)piperazinyl)-2-propylmethylether (HUHS1013),
1-(4-(2-chlorophenyl)piperazinyl)-3-(1-naphthyloxy)-propan-2-ol (HUHS1014),
1-((2-((2-methoxyphenyl)amino)ethyl)amino)-3-(1-naphthyloxyl)propan-2-ol (HUHS1015),
1-(2-methoxyphenyl)-4-(3-(1-naphthyloxyl)propyl)piperazine (HUHS1016),
1-(4-(2-methoxyphenyl)piperidin-1-yl)-3-(1-naphthyloxyl)propan-2-ol (HUHS1017),
1-(4-heptylpiperazinyl)-3-(1-naphthyloxyl)propan-2-ol (HUHS1018),
3-(1-naphthyloxy)-1-(4-octylpiperazinyl)propan-2-ol (HUHS1019),
3-(1-naphthyloxy)-1-(4-(1-naphthyl)piperazinyl)propan-2-ol (HUHS1020) or
3-(1-naphthyloxy)-1-(4-(2-naphthyl)piperazinyl)propan-2-ol (HUHS1021), or a pharmaceutically acceptable salt thereof.

[10] The compound of the above-mentioned [7], wherein the compound represented by the formula (I) is
3-(1-naphthyloxy)-1-(4-phenylpiperazinyl)propan-2-ol (HUHS1004),
1-(4-(2-methoxyphenyl)piperazinyl)-3-phenoxypropan-2-ol (HUHS1006),
1-(4-diphenylmethylpiperazinyl)-3-(1-naphthyloxy)-propan-2-ol (HUHS1011),
1-(4-(2-chlorophenyl)piperazinyl)-3-(1-naphthyloxy)-propan-2-ol (HUHS1014),
1-((2-((2-methoxyphenyl)amino)ethyl)amino)-3-(1-naphthyloxyl)propan-2-ol (HUHS1015),
1-(4-(2-methoxyphenyl)piperidin-1-yl)-3-(1-naphthyloxyl)propan-2-ol (HUHS1017),
1-(4-heptylpiperazinyl)-3-(1-naphthyloxyl)propan-2-ol (HUHS1018) or
3-(1-naphthyloxy)-1-(4-octylpiperazinyl)propan-2-ol (HUHS1019),
or a pharmaceutically acceptable salt thereof.

[11] The compound of the above-mentioned [7], wherein the compound represented by the formula (I) is 1-((2-((2-methoxyphenyl)amino)ethyl)amino)-3-(1-naphthyloxy)propan-2-ol (HUHS1015), or a pharmaceutically acceptable salt thereof.

Effect of the Invention

The aryloxy derivative provided by the present invention shows a cell proliferation suppressive action on a wide range of cancer cells, and is promising as an anti-cancer agent.

DESCRIPTION OF EMBODIMENTS

Figure 1:
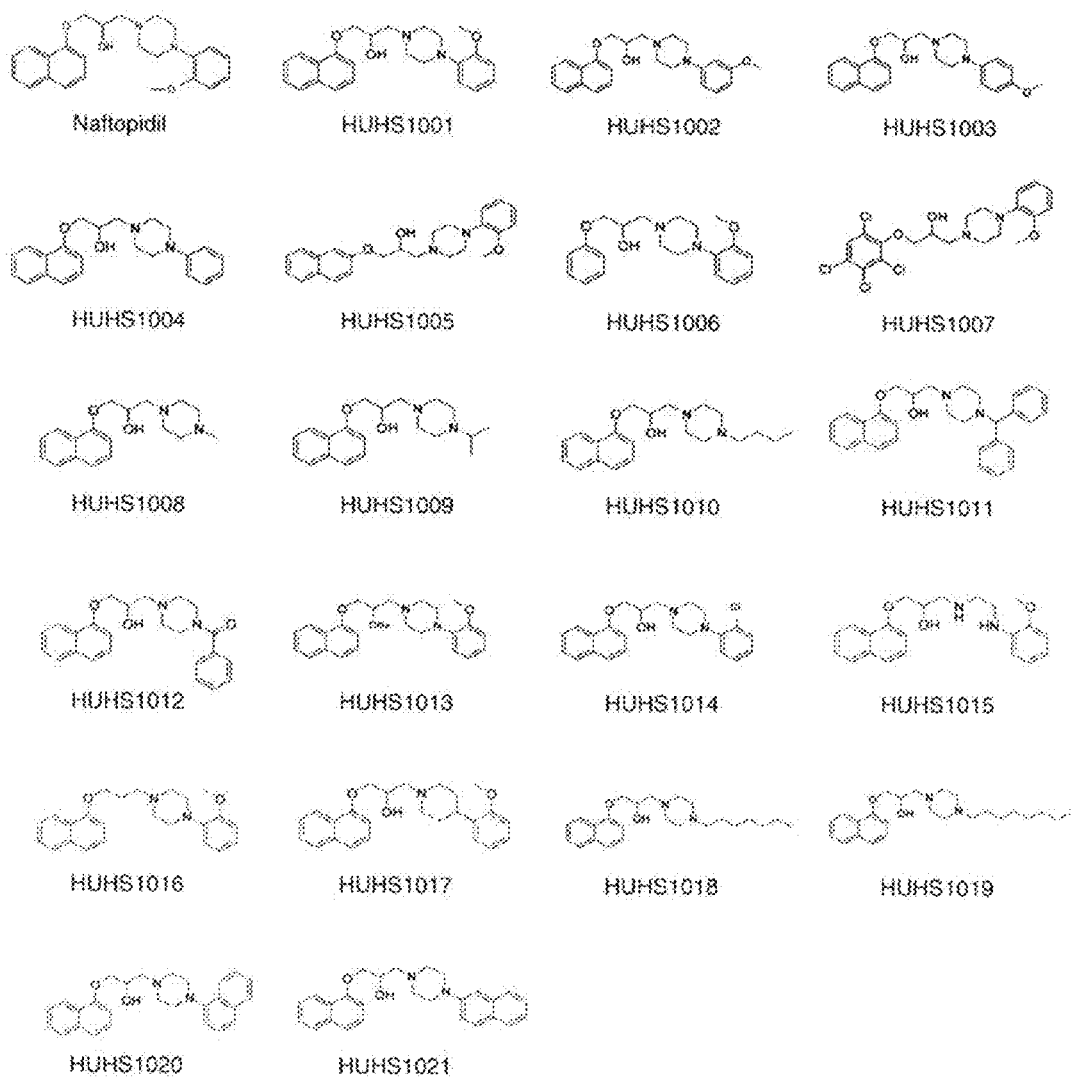
FIG. 1 shows structural formulas of naftopidil and the aryloxy derivatives of the present invention.

The meanings and definitions of the terms in the present specification are described in the following.

Examples of the "halogen atom" include a fluorine atom, a chlorine atom, a bromine atom and an iodine atom.

The "$C_{1-10}$ alkyl group" is a straight chain or branched alkyl group having 1-10 carbon atoms, and specific examples thereof include methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl, n-heptyl, 2-heptyl, n-octyl, 2-octyl, n-nonanyl, 2-nonanyl, n-decanyl, 2-decanyl and the like. The "optionally substituted $C_{1-10}$ alkyl group" is a $C_{1-10}$ alkyl group (mentioned above) optionally having substituent(s), and examples of the substituent include halogen atoms such as a fluorine atom, a chlorine atom, a bromine atom and the like, $C_{1-4}$ alkoxy groups such as methoxy, ethoxy, propyloxy, butyloxy and the like, an amino group, a hydroxyl group, a $C_{6-10}$ aryl group (mentioned below), an oxo group and the like. The "$C_{1-6}$ alkyl group" is a straight chain or branched alkyl group having 1-6 carbon atoms, and is specifically, among the aforementioned "$C_{1-10}$ alkyl group", one having 1-6 carbon atoms.

The "$C_{2-6}$ alkenyl group" is a straight chain or branched alkenyl group having 2-6 carbon atoms, and examples thereof include vinyl, allyl, propenyl, isopropenyl, butenyl, isobutenyl, but-3-en-1-yl, penta-4-en-1-yl, hexa-5-en-1-yl and the like. Of these, a vinyl group is preferable.

The "$C_{1-6}$ alkoxy group" is a straight chain or branched alkoxy group having 1-6 carbon atoms, and specific examples thereof include methoxy, ethoxy, propyloxy, isopropyloxy, butyloxy, isobutyloxy, secondary butyloxy, tertiary butyloxy, pentyloxy, hexyloxy and the like.

The "$C_{6-10}$ aryl group" is an aryl group having 6-10 carbon atoms, and specific examples thereof include phenyl, 1-naphthyl, 2-naphthyl and the like. The "optionally substituted $C_{6-10}$ aryl group" is an aryl group having 6-10 carbon atoms (mentioned above) which optionally has substituent(s). Examples of the substituent include halogen atoms such as a fluorine atom, a chlorine atom, a bromine atom and the like, $C_{1-4}$ alkoxy groups such as methoxy, ethoxy, propyloxy, butyloxy and the like, an amino group, a hydroxyl group and the like.

The "ar($C_{1-6}$ alkyl) group" is a $C_{1-6}$ alkyl group (mentioned above) substituted by an aryl group, and examples of the aryl group here include a $C_{6-10}$ aryl group (mentioned above). The "optionally substituted ar($C_{1-6}$ alkyl) group" is an ar($C_{1-6}$ alkyl) group (mentioned above) optionally having substituent(s), and the substituent may be bonded to the alkyl group moiety or the aryl group moiety. Examples of the substituent that may be bonded to the alkyl group moiety include halogen atoms such as a fluorine atom, a chlorine atom, a bromine atom and the like, $C_{1-4}$ alkoxy groups such as methoxy, ethoxy, propyloxy, butyloxy and the like, an amino group, a hydroxyl group, a $C_{6-10}$ aryl group (mentioned above), an oxo group and the like. Examples of the substituent that may be bonded to the aryl group moiety include halogen atoms such as a fluorine atom, a chlorine atom, a bromine atom and the like, $C_{1-4}$ alkoxy groups such as methoxy, ethoxy, propyloxy, butyloxy and the like, an amino group, a hydroxyl group and the like.

The present invention provides a compound represented by the following formula (I) (hereinafter to be also referred to as the compound of the present invention (I)) or a pharmaceutically acceptable salt thereof.

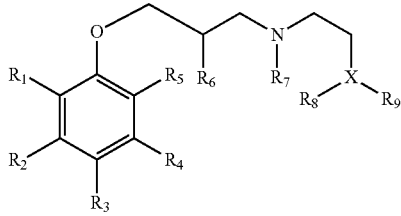

(I)

wherein
$R^1$-$R^5$ are the same or different and each is a hydrogen atom, a halogen atom, or a $C_{2-6}$ alkenyl group;
$R^1$ and $R^2$, or $R^2$ and $R^3$ optionally form a benzene ring together with a carbon atom bonded thereto;
$R^6$ is a hydrogen atom, a hydroxyl group or a $C_{1-6}$ alkoxy group;
$R^7$ and $R^8$ are the same or different and each is a hydrogen atom or a $C_{1-6}$ alkyl group;
$R^7$ and $R^8$ optionally form a ring together with a nitrogen atom bonded thereto and X;
X is CH or N;
$R^9$ is an alkyl group, an optionally substituted ar($C_{1-6}$ alkyl) group, an optionally substituted $C_{6-10}$ aryl group or an optionally substituted $C_{1-10}$ alkyl group,
(provided when $R^1$ and $R^2$ form a benzene ring together with a carbon atom bonded thereto, $R^7$ and $R^8$ form a ring together with a nitrogen atom bonded thereto and X, and $R^6$ is a hydroxyl group, then $R^9$ is not a phenyl group substituted by a methoxy group).

As the halogen atom for $R^1$-$R^5$, a chlorine atom is preferable.

$R^1$-$R^5$ are preferably the same or different and each is a hydrogen atom or a $C_2$-6 alkenyl group, more preferably, $R^1$ and $R^2$ are vinyl, and form a benzene ring together with a carbon atom bonded thereto, and $R^3$-$R^5$ are hydrogen atoms.

As the $C_{1-6}$ alkoxy group for $R^6$, methoxy is preferable.

$R^6$ is preferably a hydroxyl group.

As the $C_{1-6}$ alkyl group for $R^7$ or $R^8$, methyl is preferable.

$R^7$ and $R^8$ are preferably both hydrogen atoms. When $R^7$ and $R^8$ are both hydrogen atoms, X is preferably N.

Furthermore, in another preferable embodiment of $R^7$ and $R^8$, they are each methyl and form a ring together with a nitrogen atom bonded thereto and X. Examples of the ring formed by $R^7$ and $R^8$ together with a nitrogen atom bonded thereto and X include a pyridine ring (when X is CH) and a piperidine ring (when X is N), and they are also preferable.

As the optionally substituted $C_{6-10}$ aryl group for $R^9$, optionally substituted phenyl and naphthyl are preferable. Here, as the substituent, a halogen atom (preferably a chlorine atom) and a $C_{1-4}$ alkoxy group (preferably methoxy) are preferable. Particularly preferably, $R^9$ is phenyl having a methoxy group at the 2-position.

As the substituent of the optionally substituted $C_{1-10}$ alkyl group for $R^9$, a $C_{6-10}$ aryl group (preferably phenyl) and an oxo group are preferable.

As the optionally substituted ar($C_{1-6}$ alkyl) group for $R^9$, optionally substituted benzyl is preferable.

Examples of preferable compound (I) of the present invention include the following compounds.

3-(1-naphthyloxy)-1-(4-phenylpiperazinyl)propan-2-ol (HUHS1004),
1-(4-(2-methoxyphenyl)piperazinyl)-3-phenoxypropan-2-ol (HUHS1006),
1-(4-(2-methoxyphenyl)piperazinyl)-3-(2,3,4,6-tetrachlorophenoxyl)propan-2-ol (HUHS1007),
1-(4-methylpiperazinyl)-3-(1-naphthyloxy)propan-2-ol (HUHS1008),
1-(4-isopropylpiperazinyl)-3-(1-naphthyloxy)propan-2-ol (HUHS1009),
3-(1-naphthyloxy)-1-(4-propylpiperazinyl)propan-2-ol (HUHS1010),
1-(4-diphenylmethylpiperazinyl)-3-(1-naphthyloxy)-propan-2-ol (HUHS1011),
3-(1-naphthyloxy)-1-(4-(phenylcarbonyl)piperazinyl)propan-2-ol (HUHS1012),
3-(1-naphthyloxy)-1-(4-(2-methoxyphenyl)piperazinyl)-2-propylmethylether (HUHS1013),
1-(4-(2-chlorophenyl)piperazinyl)-3-(1-naphthyloxy)-propan-2-ol (HUHS1014),
1-((2-((2-methoxyphenyl)amino)ethyl)amino)-3-(1-naphthyloxy)propan-2-ol (HUHS1015),
1-(2-methoxyphenyl)-4-(3-(1-naphthyloxy)propyl)piperazine (HUHS1016),
1-(4-(2-methoxyphenyl)piperidin-1-yl)-3-(1-naphthyloxy)propan-2-ol (HUHS1017),
1-(4-heptylpiperazinyl)-3-(1-naphthyloxyl)propan-2-ol (HUHS1018),
3-(1-naphthyloxy)-1-(4-octylpiperazinyl)propan-2-ol (HUHS1019),
3-(1-naphthyloxy)-1-(4-(1-naphthyl)piperazinyl)propan-2-ol (HUHS1020),
3-(1-naphthyloxy)-1-(4-(2-naphthyl)piperazinyl) propan-2-ol (HUHS1021).

Preferred are HUHS1004, HUHS1006, HUHS1007, HUHS1011, HUHS1012, HUHS1013, HUHS1014, HUHS1015, HUHS1016, HUHS1017, HUHS1018, HUHS1019, HUHS1020 and HUHS1021, and more preferred are HUHS1004, HUHS1006, HUHS1011, HUHS1014, HUHS1015, HUHS1017, HUHS1018 and HUHS1019. Still more preferred is 1-((2-((2-methoxyphenyl)amino)ethyl)amino)-3-(1-naphthyloxy)propan-2-ol (HUHS1015).

The compound (I) of the present invention may be in the form of a salt. Examples of such salt include a metal salt, an ammonium salt, salts with organic bases, salts with inorganic acids, salts with organic acids, salts with basic or acidic amino acids and the like. Preferable examples of the metal salt include alkali metal salts such as sodium salt, potassium salt and the like; alkaline earth metal salts such as calcium salt, magnesium salt, barium salt and the like; aluminum salt and the like. Preferable examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salts with inorganic acids include salts with hydrochloric acid, hydrobromic acid, nitric acid, sulfuric acid, phosphoric acid and the like. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acids include salts with arginine, lysine, ornithine and the like. Preferable examples of the salts with acidic amino acids include salts with aspartic acid, glutamic acid and the like.

Of these, pharmaceutically acceptable salts are preferable. For example, when the compound has an acidic functional group, inorganic salts such as alkali metal salts (e.g., sodium salt, potassium salt etc.), alkaline earth metal salts (e.g., calcium salt, magnesium salt, barium salt etc.) and the like, ammonium salt and the like are preferable. When the compound has a basic functional group, for example, salts with inorganic acids such as hydrochloric acid, hydrobromic acid, nitric acid, sulfuric acid and phosphoric acid, and salts with organic acids such as acetic acid, phthalic acid, fumaric acid, oxalic acid, tartaric acid, maleic acid, citric acid, succinic acid, methanesulfonic acid, p-toluenesulfonic acid and the like are preferable.

Hereinafter the compound of the present invention (I) and a pharmaceutically acceptable salt thereof are sometimes generically referred to as the compound of the present invention.

When the compound of the present invention has isomers such as optical isomer, stereoisomer, positional isomer, rotamer and the like, any one isomer and a mixture of isomers are also encompassed in the compound of the present invention. For example, when an optical isomer is present in the compound of the present invention, an optical isomer resolved from a racemate is also encompassed in the compound of the present invention. These isomers can be each obtained as a single product by a synthesis means and a separation means (concentration, solvent extraction, column chromatography, recrystallization etc.) known per se.

The compound of the present invention may be in the form of a crystal or an amorphous form. When the compound of the present invention is a crystal, it is encompassed in the compound of the present invention even when it is a single crystal of a mixture of crystal forms. The crystal can be produced by crystallization by applying a crystallization method known per se.

The compound of the present invention may be a solvate (e.g., hydrate etc.) or non-solvate, both of which are encompassed in the compound of the present invention.

The compound of the present invention may be labeled with an isotope (e.g., $^3$H, $^{14}$C, $^{35}$S, $^{125}$I etc.) and the like.

The compound of the present invention has a growth suppressive action on various cancer cells. Having such action, the compound of the present invention is useful as an anti-cancer agent for mammals (e.g., human, monkey, cat, swine, horse, bovine, mouse, rat, guinea pig, dog, rabbit etc.).

Examples of the target cancer include acute myeloid leukemia, acute lymphocytic leukemia, malignant lymphoma, villous cancer, multiple myeloma, soft tissue tumor, chronic myeloid leukemia, medullary thyroid carcinoma, osteosarcoma, mesothelioma, cervical cancer, esophagus cancer, lung cancer, colorectal cancer, gastric cancer, biliary cancer, brain tumor, malignant melanoma, kidney cancer, pancreatic cancer, liver cancer, bladder cancer and the like. Preferred as the target disease are mesothelioma, lung cancer, liver cancer, gastric cancer and bladder cancer.

The content of the compound of the present invention in an anti-cancer agent containing the compound of the present invention as an active ingredient is generally about 0.01—about 99.9 wt %, preferably about 0.1—about 50 wt %, relative to the whole preparation.

The dose of the compound of the present invention is determined according to the age, body weight, general health condition, sex, meal, an administration time, administration method, clearance rate, combination of drugs, and the level of the disease state of the patient undergoing the treatment thereof, and in consideration of these or other factors.

While the dose varies depending on the target disease, symptom, administration subject, administration method and the like, for example, the daily dose of compound (I) of the present invention to an adult (body weight 60 kg) is generally about 30-100 mg by oral administration, about 0.3-1 mg by intravenous administration, and about 3-10 mg by intramuscular administration, which is administered singly or in plural (e.g., 2 or 3) portions per day. Where necessary, a weekly dose can also be administered singly or in plural portions (e.g., 2 or 3 portions per week).

To obtain a desired effect, the compound of the present invention can be administered singly or used in an appropriate combination with other anti-cancer agents.

Examples of other anti-cancer agent include metabolic antagonists (e.g., methotrexate, 5-fluorouracil etc.), alkylating agents (e.g., cyclophosphamide, ifosfamide etc.), platinum anti-cancer agents (e.g., cisplatin, carboplatin etc.), topoisomerase inhibitors (e.g., etoposide etc.), antitumor antibiotics (e.g., mitomycin, adriamycin etc.), plant-derived antitumor agents (e.g., vincristine, vindesine, taxol etc.), tyrosine kinase inhibitors (e.g., gefitinib, imatinib etc.), humanized antibodies (e.g., herceptin etc.) and the like.

The compound of the present invention or a salt thereof is blended with a pharmaceutically acceptable carrier, and can be appropriately formulated as solid preparations such as tablet, capsule, granule, powder and the like; liquid preparations such as syrup, injection and the like; percutaneous absorption agents such as adhesive preparation, ointment, plaster and the like; inhalant; and suppository.

A medicament containing the compound of the present invention may be administered orally or parenterally. The above-mentioned compound may be used alone, or two or more kinds thereof may be used in combination.

As a pharmaceutically acceptable carrier, various organic or inorganic carrier substances, which are conventionally used as preparation materials, can be used. Specifically, an excipient, a lubricant, a binder, a disintegrant for solid preparations, and a solvent, a solubilizing agent, a suspending agent, an isotonic agent, a buffering agent, a soothing agent and the like for liquid preparations can be added. In addition, preparation additives such as preservative, antioxidant, colorant, sweetening agent and the like can also be used as necessary.

Examples of the excipient include lactose, sucrose, glucose, starch, saccharose, crystalline cellulose, *Glycyrrhiza uralensis*, mannitol, sodium hydrogen carbonate, calcium phosphate, calcium sulfate and the like.

Examples of the lubricant include magnesium stearate, stearic acid, calcium stearate, purification talc, colloidal silica and the like.

Examples of the binder include crystalline cellulose, sucrose, mannitol, dextrin, hydroxypropylcellulose, hydroxypropylmethylcellulose, polyvinylpyrrolidone and the like.

Examples of the disintegrant include starch, carboxymethylcellulose, calcium carboxymethylcellulose, croscarmellose sodium, sodium carboxymethyl starch and the like.

Preferable examples of the solvent include water for injection, alcohol, propylene glycol, macrogol, sesame oil, corn oil and the like.

Preferable examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyltriethanolamine, sodium lauryl sulfate, lauryl aminopropionic acid, lecithin, benzalkonium chloride, benzethonium chloride, glycerol monostearate and the like; polyvinyl alcohol, polyvinylpyrrolidone, sodium carboxymethylcellulose, methylcellulose, hydroxymethylcellulose, hydroxyethylcellulose, hydroxypropylcellulose and the like.

Preferable examples of the isotonic agent include sodium chloride, glycerol, D-mannitol and the like.

Preferable examples of the buffering agent include buffers such as phosphate, acetate, carbonate, citrate, etc. and the like.

Preferable examples of the soothing agent include benzylalcohol and the like.

Preferable examples of the preservative include paraoxybenzoates, chlorobutanol, benzyl alcohol, phenethyl alcohol, dehydroacetic acid, sorbic acid and the like.

Preferable examples of the antioxidant include sulfite, ascorbic acid and the like.

Preferable examples of the colorant include tar pigment, caramel, red ferric oxide, titanium oxide, riboflavins and the like.

Preferable examples of the sweetening agent include glucose, fructose, invert sugar, sorbitol, xylitol, glycerol, simple syrup and the like.

Production Method

The production method of the compound of the present invention is explained below.

The compound of the present invention can be appropriately prepared by various methods, may be chemically synthesized, or can be obtained by appropriately modifying naftopidil as necessary, which is a known compound. The production method of naftopidil is disclosed in JP-A-SHOU50-121286.

In addition, the compound of the present invention can be produced by the method shown below, a method analogous thereto and the like.

As starting compounds, unless particularly indicated, commercially available products are easily available, or can be produced according to a method known per se or a method analogous thereto.

In each reaction and each reaction for the synthesis of the starting compounds, generally-known solvents are sometimes used in the reaction.

Examples of the generally-known solvent include ethers such as tetrahydrofuran, diethyl ether, 1,2-dimethoxyethane, 1,4-dioxane and the like, esters such as ethyl acetate, butyl acetate and the like, aromatic hydrocarbons such as benzene, toluene and the like, aromatic heterocycle compounds such as pyridine, lutidine and the like, amides such as N,N-dimethylformamide, N-methylpyrrolidone and the like, halides such as chloroform, methylene chloride and the like, alcohols such as methanol, ethanol, 2-propanol, 2,2-dimethylethanol and the like, hydrocarbon compounds such as hexane, heptane, petroleum ether and the like, carboxylic acids such as formic acid, acetic acid and the like, water and the like.

As a solvent to be used in the reaction may be a single solvent or a mixture of 2 to 6 kinds of solvents.

The reaction is sometimes performed in the co-presence of, for example, amines such as triethylamine, N,N-diisopropylamine, pyridine, N-methylmorpholine and the like, and bases such as sodium hydroxide, potassium carbonate, sodium hydride and the like.

The reaction is sometimes performed in the co-presence of, for example, acids such as hydrochloric acid, sulfuric acid, acetic acid and the like.

Synthesis Method 1: Formula (I) Wherein $R^6$ is OH [Synthesis of Compound (I-1)]

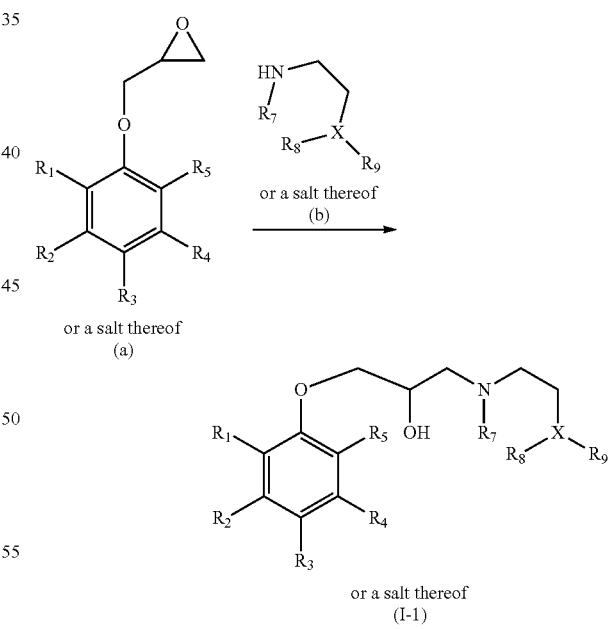

wherein each symbol is as defined above.

The method is a nucleophilic substitution reaction of compound (a) and compound (b). This reaction is generally performed in a conventional solvent that does not adversely influence the reaction. The reaction temperature is not particularly limited, and the reaction is generally performed under warming or heating. The reaction time is generally several hours.

Synthesis Method 2: Formula (I) Wherein $R^6$ is a Lower Alkoxy Group [Synthesis of Compound (I-2)]

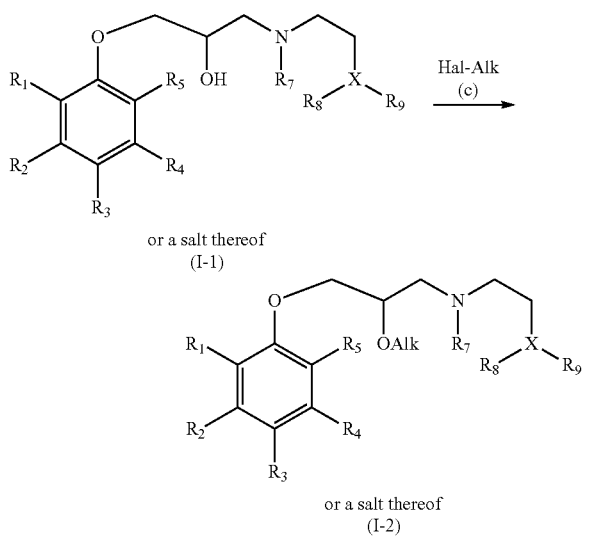

or a salt thereof
(I-1)

or a salt thereof
(I-2)

wherein each symbol is as defined above.

In this method, compound (I-1) obtained by the above-mentioned synthesis method 1 is reacted with alkyl halide (Hal-Alk; (c)) in the presence of a base to alkylate a hydroxyl group in compound (I-1) to convert same to an alkoxy group. The reaction temperature is generally 0° C.—room temperature, and the reaction time is generally several hours. Examples of the alkyl halide include alkyl having 1-6 carbon atoms and substituted by a chlorine atom, a bromine atom or an iodine atom. Specific examples thereof include methyl iodide, ethyl bromide, isopropyl bromide, ethylene dibromide, isopropyl chloride and the like.

Synthesis Method 3:

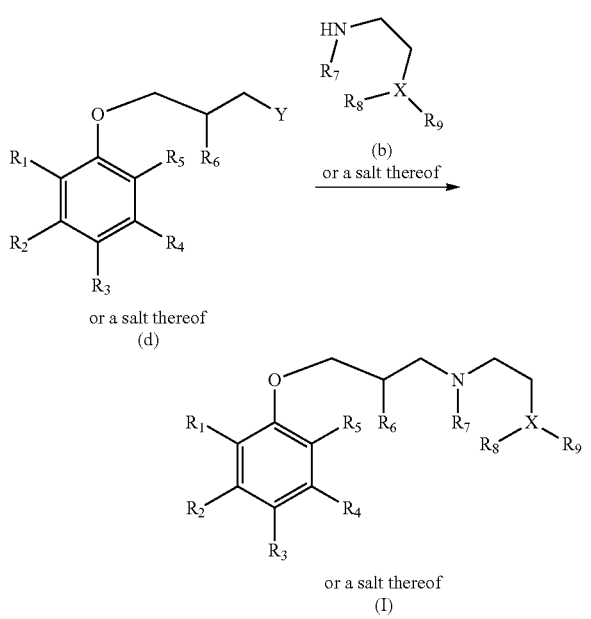

or a salt thereof
(d)

or a salt thereof
(I)

wherein Y is a mesyl group, a tosyl group, a trifluoromethanesulfonyl group or halogen, and each of other symbols is as defined above.

This method is a nucleophilic substitution reaction of compound (d) and compound (b). This reaction is generally performed in a conventional solvent that does not adversely influence the reaction. The reaction temperature is not particularly limited, and the reaction is generally performed under warming or heating. The reaction time is generally several hours.

The present invention is explained in detail in the following by referring to Examples and Experimental Examples, which are mere examples and do not limit the present invention. The present invention may be changed within the range that does not deviate from the scope of the present invention.

EXAMPLES

Reference Example 1

Synthesis of (RS)-naftopidil (HUHS1001)

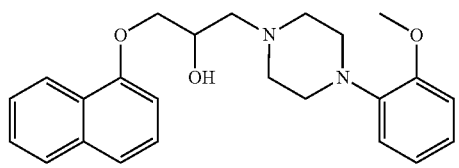 [SMILES: COc1ccccc1N1CCN(CC(O)COc2cccc3ccccc23)CC1]

To a solution of 2-((1-naphthyloxy)methyl)oxirane (100 mg, 0.50 mmol) in ethanol (1 mL) was added 4-(2-methoxyphenyl)piperazine (95 μL, 0.60 mmol) at room temperature. The mixture was stirred under reflux for 1 hr. The reaction mixture was concentrated under reduced pressure. The crude product was purified by silica gel column chromatography to give (RS)-naftopidil (199 mg, 100%).

$^1$H-NMR (400 MHz, CDCl$_3$) δ 2.72-2.76 (m, 4H), 2.92-2.95 (m, 2H), 3.09-3.18 (m, 4H), 3.87 (s, 3H), 4.16 (dd, J=9.6 and 5.0 Hz, 1H), 4.24 (dd, J=9.6 and 5.0 Hz, 1H), 4.28-4.34 (m, 1H), 6.84 (d, J=7.8 Hz, 1H), 6.87 (d, J=7.8 Hz, 1H), 6.91-6.98 (m, 2H), 7.00-7.04 (m, 1H), 7.39 (t, J=8.2 Hz, 1H), 7.44 (d, J=8.2 Hz, 1H), 7.47-7.51 (m, 2H), 7.79-7.81 (m, 1H), 8.26-8.29 (m, 1H); ESI-HRMS (positive ion, sodium formate) calcd. for $C_{24}H_{29}N_2O_3$ ([M+H$^+$]): 393.2173. Found 393.2148.

Reference Example 2

1-(4-(3-methoxyphenyl)piperazinyl)-3-(1-naphthyloxyl)propan-2-ol (HUHS1002)

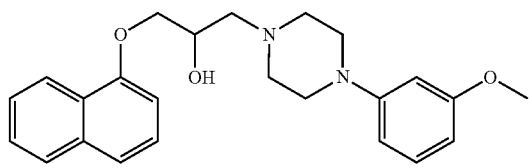 [SMILES: COc1cccc(N2CCN(CC(O)COc3cccc4ccccc34)CC2)c1]

To a solution of 2-((1-naphthyloxy)methyl)oxirane (100 mg, 0.50 mmol) in ethanol (1 mL) was added 4-(3-methoxyphenyl)piperazine (104 μL, 0.60 mmol) at room temperature. The mixture was stirred under reflux for 1 hr. The reaction mixture was concentrated under reduced pressure. The crude product was purified by silica gel column chromatography to give HUHS1002 (165 mg, 84%).

¹H-NMR (400 MHz, CDCl₃) δ2.63-2.77 (m, 4H), 2.84-2.89 (m, 2H), 3.19-3.28 (m, 4H), 3.79 (s, 3H), 4.16 (dd, J=9.6 and 5.0 Hz, 1H), 4.24 (dd, J=9.6 and 5.0 Hz, 1H), 4.27-4.33 (m, 1H), 6.43 (dd, J=8.2 and 1.8 Hz, 1H), 6.48 (t, J=1.8 Hz, 1H), 6.56 (dd, J=8.2 and 1.8 Hz, 1H), 6.84 (d, J=6.8 Hz, 1H), 7.18 (t, J=8.2 Hz, 1H), 7.37 (t, J=8.2 Hz, 1H), 7.45 (d, J=8.2 Hz, 1H), 7.45-7.51 (m, 2H), 7.78-7.81 (m, 1H), 8.25-8.28 (m, 1H); ESI-HRMS (positive ion, sodium formate) calcd. for C₂₄H₂₉N₂O₃ ([M+H⁺]): 393.2173. Found 393.2149.

Reference Example 3

1-(4-(4-methoxyphenyl)piperazinyl)-3-(1-naphthyloxyl)propan-2-ol (HUHS1003)

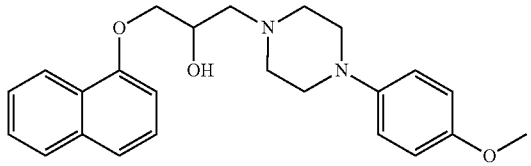 [SMILES: COc1ccc(N2CCN(CC(O)COc3cccc4ccccc34)CC2)cc1]

To a solution of 2-((1-naphthyloxy)methyl)oxirane (75 mg, 0.38 mmol) in ethanol (1 mL) were added 4-(4-methoxyphenyl)piperazine (119 mg, 0.45 mmol) and diisopropylethylamine (0.19 mL, 1.12 mmol) at room temperature. The mixture was stirred under reflux for 1 hr. The reaction mixture was concentrated under reduced pressure. The crude product was purified by silica gel column chromatography to give HUHS1003 (104 mg, 72%).

¹H-NMR (400 MHz, CDCl₃) δ2.66-2.71 (m, 2H), 2.73-2.76 (m, 2H), 2.87-2.92 (m, 2H), 3.09-3.19 (m, 4H), 3.77 (s, 3H), 4.16 (dd, J=9.6 and 5.0 Hz, 1H), 4.24 (dd, J=9.6 and 5.0 Hz, 1H), 4.28-4.34 (m, 1H), 6.84-6.87 (m, 3H), 6.91-6.92 (m, 2H), 7.37 (t, J=8.2 Hz, 1H), 7.44-7.51 (m, 3H), 7.78-7.95 (m, 1H), 8.23-8.30 (m, 1H); ESI-HRMS (positive ion, sodium formate) calcd. for C₂₄H₂₉N₂O₃ ([M+H⁺]): 393.2173. Found 393.2170.

Example 1

3-(1-naphthyloxy)-1-(4-phenylpiperazinyl)propan-2-ol (HUHS1004)

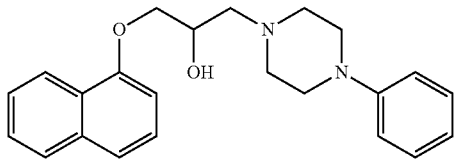 [SMILES: OC(COc1cccc2ccccc12)CN1CCN(c2ccccc2)CC1]

To a solution of 2-((1-naphthyloxy)methyl)oxirane (100 mg, 0.50 mmol) in ethanol (1 mL) was added 4-phenylpiperazine (92 μL, 0.60 mmol) at room temperature. The mixture was stirred under reflux for 1 hr. The reaction mixture was concentrated under reduced pressure. The crude product was purified by silica gel column chromatography to give HUHS1004 (180 mg, 98%).

¹H-NMR (400 MHz, CDCl₃) δ2.65-2.71 (m, 2H), 2.73-2.76 (m, 2H), 2.87-2.92 (m, 2H), 3.20-3.29 (m, 4H), 4.16 (dd, J=9.6 and 5.0 Hz, 1H), 4.25 (dd, J=9.6 and 5.0 Hz, 1H), 4.28-4.34 (m, 1H), 6.84 (d, J=7.8 Hz, 1H), 6.86 (t, J=7.3 Hz, 1H), 6.95 (d, J=8.2 Hz, 2H), 7.28 (dd, J=8.3 and 7.3 Hz, 2H), 7.37 (t, J=7.3 Hz, 1H), 7.44 (d, J=8.2 Hz, 1H) 7.43-7.51 (m, 2H), 7.79-7.82 (m, 1H), 8.26-8.28 (m, 1H); ESI-HRMS (positive ion, sodium formate) calcd. for C₂₃H₂₇N₂O₂ ([M+H⁺]): 363.2067. Found 363.2039.

Reference Example 4

1-(4-(2-methoxyphenyl)piperazinyl)-3-(2-naphthyloxyl)propan-2-ol (HUHS1005)

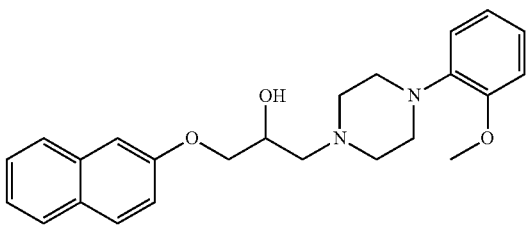 [SMILES: COc1ccccc1N1CCN(CC(O)COc2ccc3ccccc3c2)CC1]

To a solution of 2-((2-naphthyloxy)methyl)oxirane (75 mg, 0.38 mmol) in ethanol (0.75 mL) was added 4-(2-methoxyphenyl)piperazine (79 uL, 0.45 mmol) at room temperature. The mixture was stirred under reflux for 1 hr. The reaction mixture was concentrated under reduced pressure. The crude product was purified by silica gel column chromatography to give HUHS1005 (149 mg, 100%).

¹H-NMR (400 MHz, CDCl₃) δ 2.64-2.73 (m, 4H), 2.91-2.95 (m, 2H), 3.14 (m, 4H), 3.87 (s, 3H), 4.14 (d, J=5.0 Hz, 2H), 4.20-4.26 (m, 1H), 6.86-6.89 (m, 1H), 6.91-6.97 (m, 2H), 7.00-7.04 (m, 1H), 7.17 (d, J=2.3 Hz, 1H), 7.20 (dd, J=9.0 and 2.3 Hz, 1H), 7.34 (td, J=7.3 and 1.4 Hz, 1H), 7.44 (td, J=8.3 and 0.92, 1H), 7.72-7.78 (m, 3H); ESI-HRMS (positive ion, sodium formate) calcd. for C₂₄H₂₉N₂O₃ ([M+H⁺]): 393.2173. Found 393.2189.

Example 2

1-(4-(2-methoxyphenyl)piperazinyl)-3-phenoxypropan-2-ol (HUHS1006)

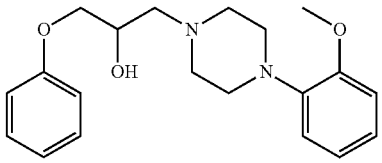 [SMILES: COc1ccccc1N1CCN(CC(O)COc2ccccc2)CC1]

To a solution of 2-(phenoxymethyl)oxirane (70 mg, 0.47 mmol) in ethanol (1 mL) was added 4-(2-methoxyphenyl)piperazine (98 μL, 0.56 mmol) at room temperature. The mixture was stirred under reflux for 1 hr. The reaction mixture was concentrated under reduced pressure. The crude product was purified by silica gel column chromatography to give HUHS1006 (107 mg, 67%).

¹H-NMR (600 MHz, CDCl₃) δ 2.61 (dd, J=12.3 and 4.0 Hz, 1H), 2.66 (dd, J=12.3 and 9.7 Hz, 1H), 2.65-2.70 (m, 2H), 2.90 (br s, 2H), 3.05-3.20 (m, 4H), 3.87 (s, 3H), 4.02 (d, J=6.0 Hz, 2H), 4.14-4.17 (m, 1H), 6.87 (dd, J=7.9 and 1.2 Hz, 1H), 6.92-6.97 (m, 5H), 7.00-7.03 (m, 1H), 7.26-7.30 (m, 2H);

ESI-HRMS (positive ion, sodium formate) calcd. for $C_{20}H_{27}N_2O_3$ ([M+H]$^+$): 343.2016. Found 343.1984.

Example 3

1-(4-(2-methoxyphenyl)piperazinyl)-3-(2,3,4,6-tetrachlorophenoxyl)propan-2-ol (HUHS1007)

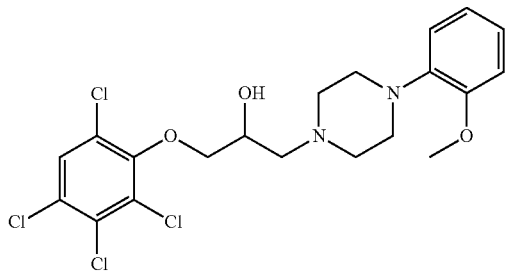 [SMILES: COc1ccccc1N1CCN(CC(O)COc2c(Cl)cc(Cl)c(Cl)c2Cl)CC1]

To a solution of 2-((2,3,4,6-tetrachlorophenoxy)methyl)oxirane (45 mg, 0.16 mmol) in ethanol (0.50 mL) was added 4-(2-methoxyphenyl)piperazine (33 µL, 0.19 mmol) at room temperature. The mixture was stirred under reflux for 1 hr. The reaction mixture was concentrated under reduced pressure. The crude product was purified by silica gel column chromatography to give HUHS1007 (34 mg, 44%).

$^1$H-NMR (400 MHz, CDCl$_3$) δ 2.65-2.75 (m, 4H), 2.88-2.92 (m, 2H), 3.08-3.17 (m, 4H), 3.87 (s, 3H), 4.07 (dd, J=9.6 and 5.5 Hz, 1H), 4.12 (dd, J=9.6 and 4.1 Hz, 1H), 4.16-4.22 (m, 1H), 6.86-6.91 (m, 1H), 6.93-6.96 (m, 2H), 6.99-7.04 (m, 1H), 7.47 (s, 1H); ESI-HRMS (positive ion, sodium formate) calcd. for $C_{20}H_{23}Cl_4N_2O_3$ ([M+H]$^+$): 481.0430. Found 481.0417.

Example 4

1-(4-methylpiperazinyl)-3-(1-naphthyloxyl)propan-2-ol (HUHS1008)

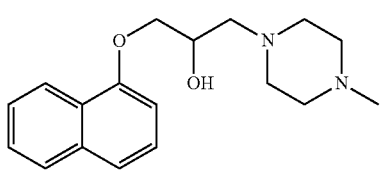 [SMILES: CN1CCN(CC(O)COc2cccc3ccccc23)CC1]

To a solution of 2-((1-naphthyloxy)methyl)oxirane (50 mg, 0.25 mmol) in ethanol (0.50 mL) was added 4-methylpiperazine (33 µL, 0.30 mmol) at room temperature. The mixture was stirred under reflux for 1 hr. The reaction mixture was concentrated under reduced pressure. The crude product was purified by silica gel column chromatography to give HUHS1008 (46 mg, 61%).

$^1$H-NMR (400 MHz, acetone-d$_6$) δ 2.18 (s, 3H), 2.30-2.45 (m, 1H), 2.50-2.65 (m, 1H), 2.59 (dd, J=12.4 and 6.9 Hz, 1H), 2.66 (dd, J=12.4 and 5.0 Hz, 1H), 2.80-3.00 (m, 6H), 4.15 (dd, J=10.5 and 6.8 Hz, 1H), 4.22-4.28 (m, 2H), 6.97 (d, J=7.8 Hz, 1H), 7.40 (t, J=8.2 Hz, 1H), 7.45-7.51 (m, 3H), 7.84 (d, J=7.8 Hz, 1H), 8.26-8.28 (d, J=7.8 Hz, 1H); ESI-HRMS (positive ion, sodium formate) calcd. for $C_{18}H_{25}N_2O_2$ ([M+H]$^+$): 301.1911. Found 301.1929.

Example 5

1-(4-isopropylpiperazinyl)-3-(1-naphthyloxyl)propan-2-ol (HUHS1009)

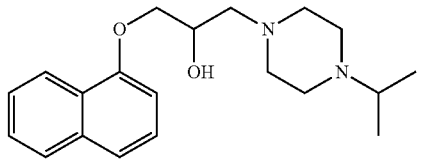 [SMILES: CC(C)N1CCN(CC(O)COc2cccc3ccccc23)CC1]

To a solution of 2-((1-naphthyloxy)methyl)oxirane (50 mg, 0.25 mmol) in ethanol (0.50 mL) was added 4-isopropylpiperazine (43 µL, 0.30 mmol) at room temperature. The mixture was stirred under reflux for 1 hr. The reaction mixture was concentrated under reduced pressure. The crude product was purified by silica gel column chromatography to give HUHS1009 (56 mg, 68%).

$^1$H-NMR (400 MHz, acetone-d$_6$) δ 0.99 (d, J=7.3 Hz, 6H), 2.52-2.68 (m, 7H), 2.88-2.93 (m, 4H), 4.14-4.18 (m, 1H), 4.21-4.28 (m, 2H), 6.96 (d, J=7.4 Hz, 1H), 7.37-7.52 (m, 4H), 7.82-7.86 (m, 1H), 8.29-8.32 (m, 1H); ESI-HRMS (positive ion, sodium formate) calcd. for $C_{20}H_{29}N_2O_2$ ([M+H]$^+$): 329.2224. Found 329.2239.

Example 6

3-(1-naphthyloxy)-1-(4-propylpiperazinyl)propan-2-ol (HUHS1010)

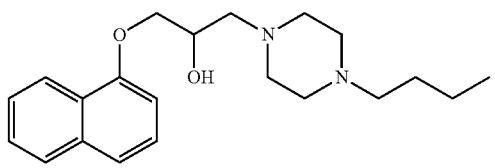 [SMILES: CCCCN1CCN(CC(O)COc2cccc3ccccc23)CC1]

To a solution of 2-((1-naphthyloxy)methyl)oxirane (50 mg, 0.25 mmol) in ethanol (0.50 mL) was added 4-propylpiperazine (44 µL, 0.30 mmol) at room temperature. The mixture was stirred under reflux for 1 hr. The reaction mixture was concentrated under reduced pressure. The crude product was purified by silica gel column chromatography to give HUHS1010 (81 mg, 95%).

$^1$H-NMR (400 MHz, acetone-d$_6$) δ 0.90 (t, J=7.6 Hz, 3H), 1.28-1.57 (m, 2H), 1.40-1.47 (m, 2H), 2.28 (t, J=7.3 Hz, 2H), 2.56-2.69 (m, 6H), 3.05 (br s, 2H), 3.31 (s, 2H), 4.15 (dd, J=10.5 and 6.8 Hz, 1H), 4.22-4.28 (m, 2H), 6.97 (d, J=7.2 Hz, 1H), 7.40 (t, J=7.3 Hz, 1H), 7.45-7.51 (m, 3H), 7.85 (dd, J=8.2 and 0.92 Hz, 1H), 8.31 (dd, J=7.8 and 0.92 Hz, 1H);

ESI-HRMS (positive ion, sodium formate) calcd. for $C_{21}H_{31}N_2O_2$ ([M+H$^+$]): 343.2380. Found 343.2340.

Example 7

1-(4-diphenylmethylpiperazinyl)-3-(1-naphthyloxy)-propan-2-ol (HUHS1011)

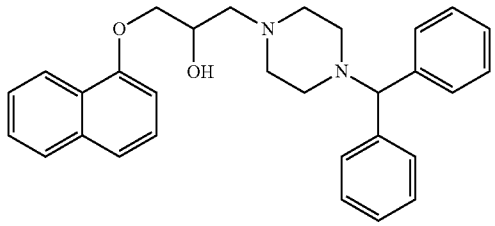 [SMILES: OC(COc1cccc2ccccc12)CN1CCN(C(c2ccccc2)c2ccccc2)CC1]

To a solution of 2-((1-naphthyloxy)methyl)oxirane (50 mg, 0.25 mmol) in ethanol (0.50 mL) was added 4-diphenylmethylpiperazine (76 mg, 0.30 mmol) at room temperature. The mixture was stirred under reflux for 1 hr. The reaction mixture was concentrated under reduced pressure. The crude product was purified by silica gel column chromatography to give HUHS1011 (98 mg, 87%).

$^1$H-NMR (400 MHz, acetone-$d_6$) δ 2.60-2.71 (m, 3H), 2.82-2.94 (m, 7H), 4.15 (dd, J=10.5 and 5.0 Hz, 1H), 4.21-4.25 (m, 2H), 4.28 (s, 1H), 6.96 (d, J=7.4 Hz, 1H), 7.18 (d, t, J=7.3 Hz, 2H), 7.29 (t, J=7.3 Hz, 4H), 7.39 (t, J=7.8 Hz, 1H), 7.44-7.51 (m, 7H), 7.83-7.85 (m, 1H), 8.80 (d, J=8.2 Hz, 1H); ESI-HRMS (positive ion, sodium formate) calcd. for $C_{30}H_{33}N_2O_2$ ([M+H$^+$]): 453.2537. Found 453.2553.

Example 8

3-(1-naphthyloxy)-1-(4-(phenylcarbonyl)piperazinyl)propan-2-ol (HUHS1012)

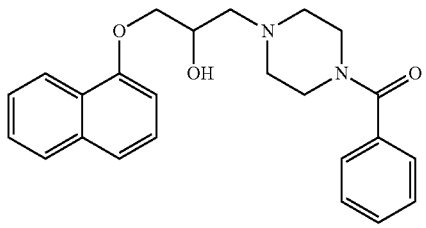 [SMILES: O=C(c1ccccc1)N1CCN(CC(O)COc2cccc3ccccc23)CC1]

To a solution of 2-((1-naphthyloxy)methyl)oxirane (50 mg, 0.25 mmol) in ethanol (0.50 mL) was added 4-(phenylcarbonyl)piperazine (57 mg, 0.30 mmol) at room temperature. The mixture was stirred under reflux for 1 hr. The reaction mixture was concentrated under reduced pressure. The crude product was purified by silica gel column chromatography to give HUHS1012 (58 mg, 59%).

$^1$H-NMR (400 MHz, CDCl$_3$) δ 2.48-2.81 (m, 6H), 3.49 (br s, 2H), 3.86 (br s, 2H), 4.14-4.18 (dd, J=10.5 and 5.0 Hz, 1H), 4.22 (dd, J=10.5 and 5.0 Hz 1H), 4.27-4.32 (m, 1H), 6.83 (d, J=7.3 Hz, 1H), 7.37 (t, J=7.8 Hz, 1H), 7.40-7.52 (m, 8H), 7.80-7.82 (m, 1H), 8.22-8.25 (m, 1H); ESI-HRMS (positive ion, sodium formate) calcd. for $C_{24}H_{27}N_2O_3$ ([M+H$^+$]): 391.2016. Found 391.2022.

Example 9

3-(1-naphthyloxy)-1-(4-(2-methoxyphenyl)piperazinyl)-2-propylmethylether (HUHS1013)

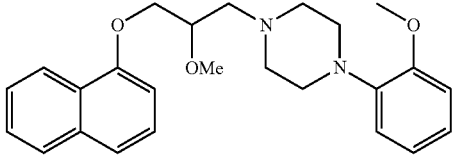

To a solution of (RS)-naftopidil (50 mg, 0.13 mmol) prepared in Reference Example 1 in DMF (1 mL) was added sodium hydride (6.1 mg, 0.15 mmol) under ice-cooling. After stirring at room temperature for 45 min, iodomethane (9.5 μL, 0.15 mmol) was added to the solution. After stirring at room temperature for 2 hr, the reaction mixture was poured into water. The aqueous layer was extracted with ethyl acetate, and the combined organic layer was dried over anhydrous MgSO$_4$ and concentrated under reduced pressure. The crude product was purified by silica gel column chromatography to give the title compound (5.5 mg, 11%).

$^1$H-NMR (400 MHz, CDCl$_3$) δ 2.75-2.78 (m, 6H), 3.08-3.13 (m, 4H), 3.60 (s, 3H), 3.87 (s, 3H), 3.91-3.96 (m, 1H), 4.23 (dd, J=9.6 Hz and 5.0 Hz, 1H), 4.33 (dd, J=9.6 and 5.0 Hz, 1H), 6.85-7.02 (m, 5H), 7.38 (t, J=7.8 Hz, 1H), 7.43-7.50 (m, 3H), 7.79-7.81 (m, 1H), 8.27-8.29 (m, 1H); ESI-HRMS (positive ion, sodium formate) calcd. for $C_{25}H_{31}N_2O_3$ ([M+H$^+$]): 407.2329. Found 407.2367.

Example 10

1-(4-(2-chlorophenyl)piperazinyl)-3-(1-naphthyloxy)-propan-2-ol (HUHS1014)

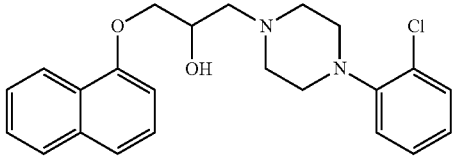 [SMILES: OC(COc1cccc2ccccc12)CN1CCN(c2ccccc2Cl)CC1]

To a solution of 2-((1-naphthyloxy)methyl)oxirane (75 mg, 0.38 mmol) in ethanol (1.5 mL) were added 4-(2-chlorophenyl)piperazine (105 mg, 0.45 mmol) and diisopropylethylamine (0.19 mL, 1.12 mmol) at room temperature. The mixture was stirred under reflux for 1 hr. The reaction mixture was concentrated under reduced pressure. The crude product was purified by silica gel column chromatography to give HUHS1014 (129 mg, 86%).

$^1$H-NMR (400 MHz, CDCl$_3$) δ 2.62-2.80 (m, 4H), 2.92-2.98 (m, 2H), 3.08-3.15 (m, 4H), 4.15 (dd, J=9.6 and 5.0 Hz, 1H), 4.25 (dd, J=9.2 and 5.2 Hz, 1H), 4.29-4.34 (m, 1H), 6.85 (d, J=7.8 Hz, 1H), 6.99 (t, J=7.8 Hz, 1H), 7.06 (d, J=7.8 Hz, 1H), 7.22 (d, J=7.8 Hz, 1H), 7.36-7.40 (m, 2H), 7.44-7.52 (m, 3H), 7.79-7.82 (m, 1H), 8.21-8.28 (m, 1H); ESI-HRMS (positive ion, sodium formate) calcd. for $C_{23}H_{25}ClN_2O_2Na$ ([M+Na$^+$]): 419.1497. Found 419.1487.

Example 11

1-((2-((2-methoxyphenyl)amino)ethyl)amino)-3-(1-naphthyloxy)propan-2-ol (HUHS1015)

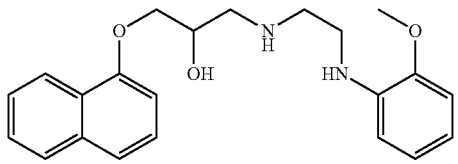 [SMILES: COc1ccccc1NCCNCC(O)COc1cccc2ccccc12]

To a solution of 2-((1-naphthyloxy)methyl)oxirane (482 mg, 2.4 mmol) in ethanol (3 mL) was added 2-((2-methoxyphenyl)amino)ethyl)amine (200 mg, 1.2 mmol) at room temperature. The mixture was stirred under reflux for 1 hr. The reaction mixture was concentrated under reduced pressure. The crude product was purified by silica gel column chromatography to give HUHS1015 (11 mg, 1.2%).

$^1$H-NMR (400 MHz, CDCl$_3$) δ 2.91-3.05 (m, 4H), 3.31 (t, J=6.0 Hz, 2H), 3.82 (s, 3H), 4.13-4.26 (m, 3H), 6.64-6.71 (m, 2H), 6.77 (d, J=7.8 Hz, 1H), 6.82 (d, J=7.8 Hz, 1H), 6.87 (t, J=7.8 Hz, 1H), 7.36 (dd, J=8.2 and 7.8 Hz, 1H), 7.43-7.50 (m, 3H), 7.80 (d, J=8.3 Hz, 1H), 8.23 (d, J=7.8 Hz, 1H); ESI-HRMS (positive ion, sodium formate) calcd. for $C_{22}H_{27}N_2O_3$ ([M+H$^+$]): 367.2016. Found 367.2054.

Example 12

1-(2-methoxyphenyl)-4-(3-(1-naphthyloxyl)propyl)piperazine (HUHS1016)

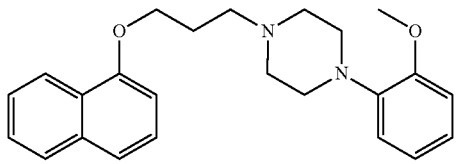 [SMILES: COc1ccccc1N1CCN(CCCOc2cccc3ccccc23)CC1]

To a solution of 3-(naphthalen-1-yloxy)propylmethanesulfonate (692 mg, 2.47 mmol) in ethanol (5 mL) was added 4-(2-methoxyphenyl)piperazine (0.53 mL, 3.0 mmol) at room temperature. The mixture was stirred under reflux for 1 hr. The reaction mixture was concentrated under reduced pressure. The crude product was purified by silica gel column chromatography to give HUHS1016 (150 mg, 16%).

$^1$H-NMR (400 MHz, CDCl$_3$) δ 2.15-2.21 (m, 2H), 2.67-2.80 (m, 6H), 3.08-3.18 (m, 4H), 3.87 (s, 3H), 4.23 (t, J=6.0 Hz, 2H), 6.82-6.87 (m, 2H), 6.92-7.03 (m, 3H), 7.34-7.50 (m, 4H), 7.78-7.80 (m, 1H), 8.25-8.28 (m, 1H); ESI-HRMS (positive ion, sodium formate) calcd. for $C_{24}H_{29}N_2O_2$ ([M+H$^+$]): 377.2224. Found 377.2226.

Example 13

1-(4-(2-methoxyphenyl)piperidin-1-yl)-3-(1-naphthyloxyl)propan-2-ol (HUHS1017)

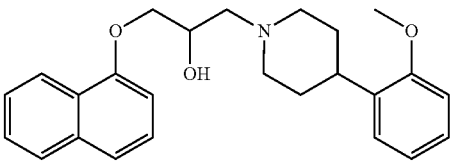

To a solution of 2-((1-naphthyloxy)methyl)oxirane (100 mg, 0.50 mmol) in ethanol (1 mL) was added 4-(2-methoxyphenyl)piperidine (116 mg, 0.60 mmol) at room temperature. The mixture was stirred under reflux for 1 hr. The reaction mixture was concentrated under reduced pressure. The crude product was purified by silica gel column chromatography to give HUHS1017 (76 mg, 39%).

$^1$H-NMR (400 MHz, CDCl$_3$) δ 1.75-1.78 (m, 4H), 2.27 (dt, J=11.7 and 2.8 Hz, 1H), 2.49-2.58 (m, 1H), 2.74 (d, J=6.9 Hz, 2H), 2.98-3.07 (m, 2H), 3.24 (d, J=11.5 Hz, 1H), 3.84 (s, 3H), 4.15 (dd, J=9.6 and 5.0 Hz, 1H), 4.25 (dd, J=9.6 and 5.0 Hz, 1H), 4.30-4.36 (m, 1H), 6.85 (t, J=7.8 Hz, 2H), 6.95 (dt, J=7.4 and 0.92 Hz, 1H), 7.18-7.23 (m, 2H), 7.37 (t, J=7.8 Hz, 1H), 7.43 (d, J=7.8 Hz, 1H), 7.45-7.52 (m, 2H), 7.78-7.82 (m, 1H), 8.25-8.28 (m, 1H); ESI-HRMS (positive ion, sodium formate). calcd. for $C_{25}H_{30}NO_3$ ([M+H$^+$]): 392.2220. Found 392.2249.

Example 14

1-(4-heptylpiperazinyl)-3-(1-naphthyloxyl)propan-2-ol (HUHS1018)

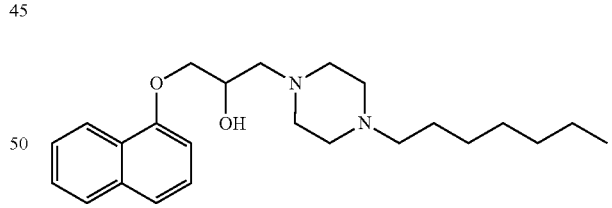

To a solution of 2-((1-naphthyloxy)methyl)oxirane (106 mg, 0.53 mmol) in ethanol (1 mL) was added 4-heptylpiperazine (118 mg, 0.64 mmol) at room temperature. The mixture was stirred under reflux for 1 hr. The reaction mixture was concentrated under reduced pressure. The crude product was purified by silica gel column chromatography to give HUHS1018 (188 mg, 93%).

$^1$H-NMR (400 MHz, CDCl$_3$) δ 0.88 (t, J=7.6 Hz, 3H), 1.20-1.40 (m, 8H), 1.44-1.57 (m, 2H), 2.30-2.35 (m, 2H), 2.35-2.60 (m, 4H), 2.60-2.70 (m, 4H), 2.75-2.85 (m, 2H), 4.15 (dd, J=10.5 and 5.0 Hz, 1H), 4.20 (dd, J=10.5 and 5.0 Hz, 1H), 4.22-4.32 (m, 1H), 6.82 (d, J=7.2 Hz, 1H), 7.38 (t, J=7.3 Hz, 1H), 7.45 (d, J=8.2 Hz, 1H), 7.45-7.55 (m, 2H), 7.84-7.86

(m, 1H), 8.23-8.35 (m, 1H); ESI-HRMS (positive ion, sodium formate) calcd. for $C_{24}H_{16}N_2O_2$ ([M+H$^+$]): 385.2861. Found 385.2861.

Example 15

3-(1-naphthyloxy)-1-(4-octylpiperazinyl)propan-2-ol (HUHS1019)

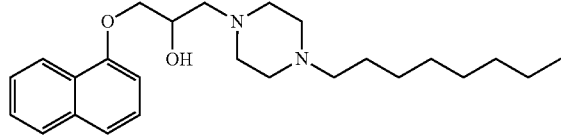 [SMILES: CCCCCCCCN1CCN(CC(O)COc2cccc3ccccc23)CC1]

To a solution of 2-((1-naphthyloxy)methyl)oxirane (10 mg, 0.50 mmol) in ethanol (1 mL) was added 4-octylpiperazine (119 mg, 0.64 mmol) at room temperature. The mixture was stirred under reflux for 1 hr. The reaction mixture was concentrated under reduced pressure. The crude product was purified by silica gel column chromatography to give HUHS1019 (155 mg, 85%).

$^1$H-NMR (400 MHz, CDCl$_3$) δ 0.88 (t, J=7.6 Hz, 3H), 1.20-1.40 (m, 10H), 1.44-1.57 (m, 2H), 2.30-2.35 (m, 2H), 2.35-2.60 (m, 4H), 2.60-2.70 (m, 4H), 2.75-2.85 (m, 2H), 4.15 (dd, J=10.5 and 5.0 Hz, 1H), 4.20 (dd, J=10.5 and 5.0 Hz, 1H), 4.22-4.32 (m, 1H), 6.82 (d, J=7.2 Hz, 1H), 7.38 (t, J=7.3 Hz, 1H), 7.45 (d, J=8.2 Hz, 1H), 7.45-7.55 (m, 2H), 7.84-7.86 (m, 1H), 8.23-8.35 (m, 1H); ESI-HRMS (positive ion, sodium formate) calcd. for $C_{25}H_{38}N_2O_2$ ([M+H$^+$]): 399.3006. Found 399.3024.

Example 16

3-(1-naphthyloxy)-1-(4-(1-naphthyl)piperazinyl)propan-2-ol (HUHS1020)

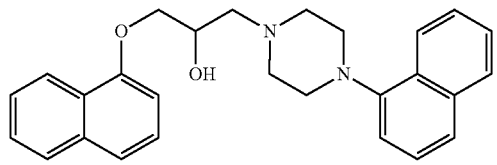 [SMILES: OC(COc1cccc2ccccc12)CN1CCN(c2cccc3ccccc23)CC1]

To a solution of 2-((1-naphthyloxy)methyl)oxirane (55 mg, 0.27 mmol) in ethanol (1 mL) was added 4-(1-naphthyl)piperazine (70 mg, 0.33 mmol) at room temperature. The mixture was stirred under reflux for 1 hr. The reaction mixture was concentrated under reduced pressure. The crude product was purified by silica gel column chromatography to give HUHS1020 (28 mg, 25%).

$^1$H-NMR (400 MHz, CDCl$_3$) 52.78-2.75 (m, 4H), 3.00-3.25 (m, 6H), 4.19 (dd, J=9.6 and 5.0 Hz, 1H), 4.28 (dd, J=9.6 and 5.0 Hz, 1H), 4.32-4.38 (m, 1H), 6.86 (d, J=7.2 Hz, 1H), 7.11 (dd, J=7.3 and 0.92 Hz, 1H), 7.37-7.58 (m, 9H), 7.80-7.84 (m, 2H), 8.19-8.22 (m, 1H), 8.28-8.30 (m, 1H); ESI-HRMS (positive ion, sodium formate) calcd. for $C_{27}H_{29}N_2O_2$ ([M+H$^+$]): 413.2224. Found 413.2222.

Example 17

3-(1-naphthyloxy)-1-(4-(2-naphthyl)piperazinyl)propan-2-ol (HUHS1021)

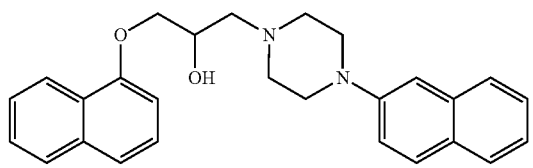 [SMILES: OC(COc1cccc2ccccc12)CN1CCN(c2ccc3ccccc3c2)CC1]

To a solution of 2-((1-naphthyloxy)methyl)oxirane (50 mg, 0.25 mmol) in ethanol (1 mL) was added 4-(2-naphthyl)piperazine (64 mg, 0.30 mmol) at room temperature. The mixture was stirred under reflux for 1 hr. The reaction mixture was concentrated under reduced pressure. The crude product was purified by silica gel column chromatography to give HUHS1021 (39 mg, 38%).

$^1$H-NMR (400 MHz, CDCl$_3$) δ 2.71-2.82 (m, 4H), 2.92-2.97 (m, 2H), 3.320-3.40 (m, 4H), 4.19 (dd, J=9.6 and 5.0 Hz, 1H), 4.27 (dd, J=9.6 and 5.0 Hz, 1H), 4.31-4.37 (m, 1H), 6.86 (d, J=7.3 Hz, 1H), 7.14 (d, J=2.3 Hz, 1H), 7.26-7.53 (m, 7H), 7.69-7.75 (m, 3H), 7.80-7.83 (m, 1H), 8.26-8.29 (m, 1H); ESI-HRMS (positive ion, sodium formate) calcd. for $C_{27}H_{29}N_2O_2$ ([M+H$^+$]): 413.2224. Found 413.2222.

Experimental Example 1

Cancer Cell Proliferation Suppressive Action of Each Naftopidil Derivative (Material and Method)
1. Naftopidil Derivative Compounds HUHS001-HUHS0021 synthesized in Reference Examples 1-4 and Examples 1-17 above were used (FIG. 1).

2. Cell Culture

NCI-H28, NCI-H2052, NCI-H2452 and MSTO-211H cells were used as human malignant pleural mesothelioma cell lines. These cells were purchased from American Type Culture Collection (Manassas, Va., USA). The cells were cultured in RPMI (Roswell Park Memorial Institute)-1640 medium added with 0.003% (W/V) L-glutamine.

A549, SBC-3 and Lu-65 cells were used as human lung cancer cell lines. These cells were purchased from Health Science Research Resources Bank (Osaka, Japan). A549 cells and SBC-3 cells were cultured in MEM (minimum essential medium) added with 0.1 mM non-essential amino acid, and Lu-65 cells were cultured in RPMI-1640 medium.

HepG2 cells and HuH-7 cells were used as human lung cancer cell lines. These cells were obtained from RIKEN cell bank (Ibaraki, Japan) and cultured in DMEM (Dulbecco's Modified Eagles Medium).

MKN-28 cells and MKN-45 cells were used as human gastric cancer cell lines. These cells were obtained from Dr. Tatematsu (Nagoya University, Japan) and cultured in RPMI-1640 medium.

253J cells, 5637 cells, KK-47 cells, TCCSUP cells, T24 cells and UM-UC-3 cells were used as human bladder cancer cell lines.

KK-47 cells were provided by Dr. Naito (Department of Urology, Kyushu University, Fukuoka, Japan). 253J cells, 5637 cells, TCCSUP cells, T24 cells and UM-UC-3 cells were purchased from American Type Culture Collection (Manassas, Va., USA). All cells were cultured in RPMI-1640 medium.

DU145 cells, LNCap cells and PC-3 cells were used as human prostate cancer cell lines. These cells were purchased from American Type Culture Collection. The DU145 cells were cultured in DMEM. The LNCaP and PC-3 cells were cultured in RPMI-1640 medium.

ACHN cells, RCC4-VHL cells and 786-O cells were used as human kidney cancer cell lines. These cells were purchased from European Collection of Animal Cell Cultures (ECACC; Salisbury, UK), and cultured in DMEM.

In all cultures, the medium was supplied with 10% (v/v) heat inactivated bovine serum, penicillin (final concentration 100 U/ml) and streptomycin (final concentration 0.1 mg/ml), and culture was performed at 37° C. under humidification atmosphere of 5% $CO_2$ and 95% air.

3. Cell Viability Assay

The cell viability was measured by a method using MTT (3-(4,5-dimethyl-2-thiazolyl)-2,5-diphenyl-2H-tetrazolium bromide) in the same manner as in a published report (Cell Physiol Biochem 2012; 30: 61-74).

(Results and Discussion)

Figure 2:
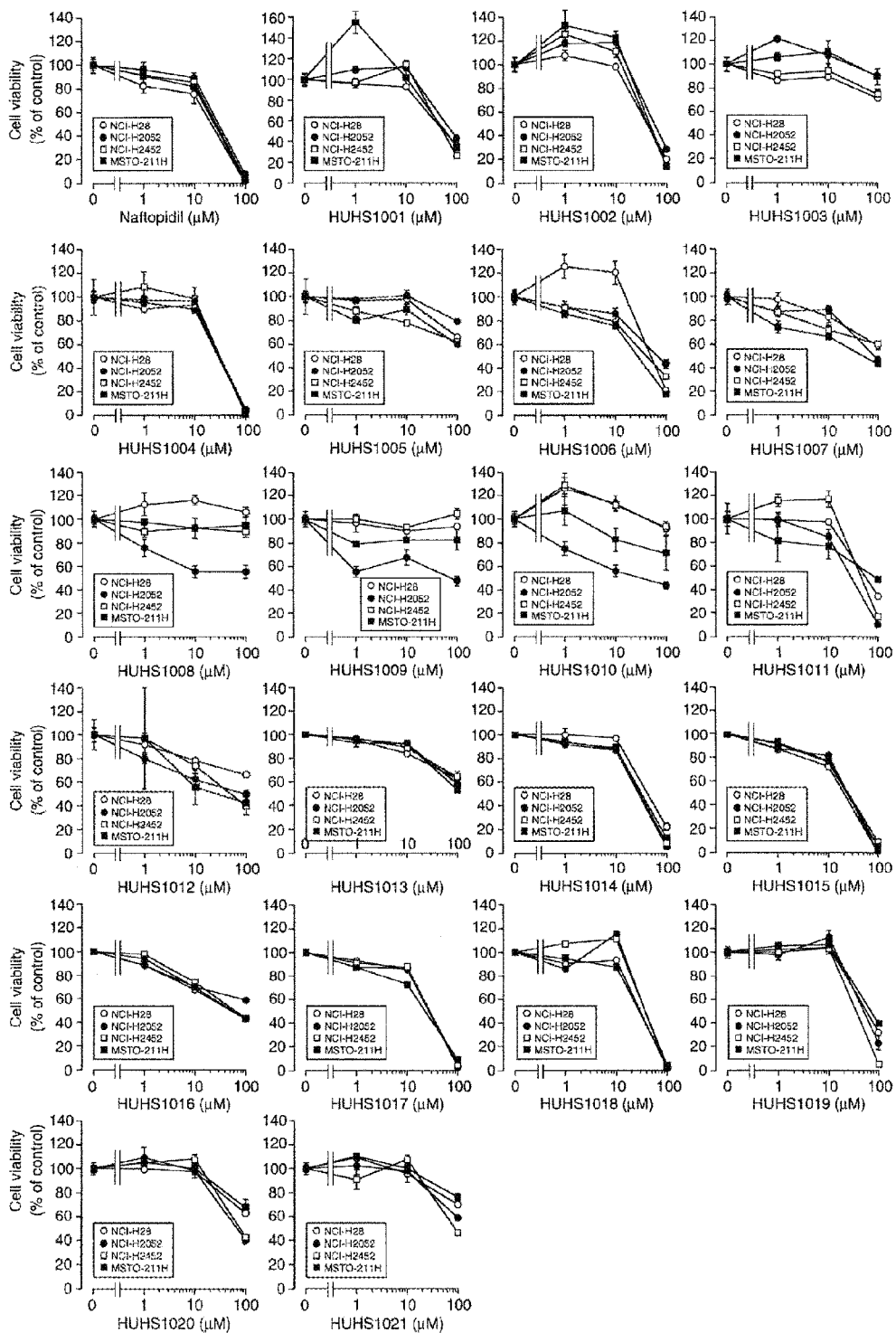
FIG. 2 shows an influence of naftopidil and the aryloxy derivatives of the present invention on the cell viability of malignant mesothelioma cells. Cancer cells (NCI-H28, NCI-H2052, NCI-H2452 and MSTO-211H) treated or not treated with a given concentration of each test compound for 24 hr were subjected to MTT assay. In the graphs, each point shows the mean ($\pm$SEM) (n=4) of % control. As a control, MTT intensity of the cells not treated with any of naftopidil and the aryloxy derivative of the present invention was used.

In all the examined malignant mesothelioma cell lines, naftopidil reduced the cell viability in a concentration dependent manner at 1-100 μM. At a concentration of 100 M, the viability was almost 0% (FIG. 2). Similarly, the aryloxy derivative of the present invention reduced the cell viability of the malignant mesothelioma cell lines in a concentration dependent manner at 1-100 μM, though the level was somewhat different (FIG. 2). Particularly, a high activity was confirmed in HUHS1002, HUHS1004, HUHS1014, HUHS1015, HUHS1017, HUHS1018 and HUHS1019 (FIG. 2).

Figure 3:
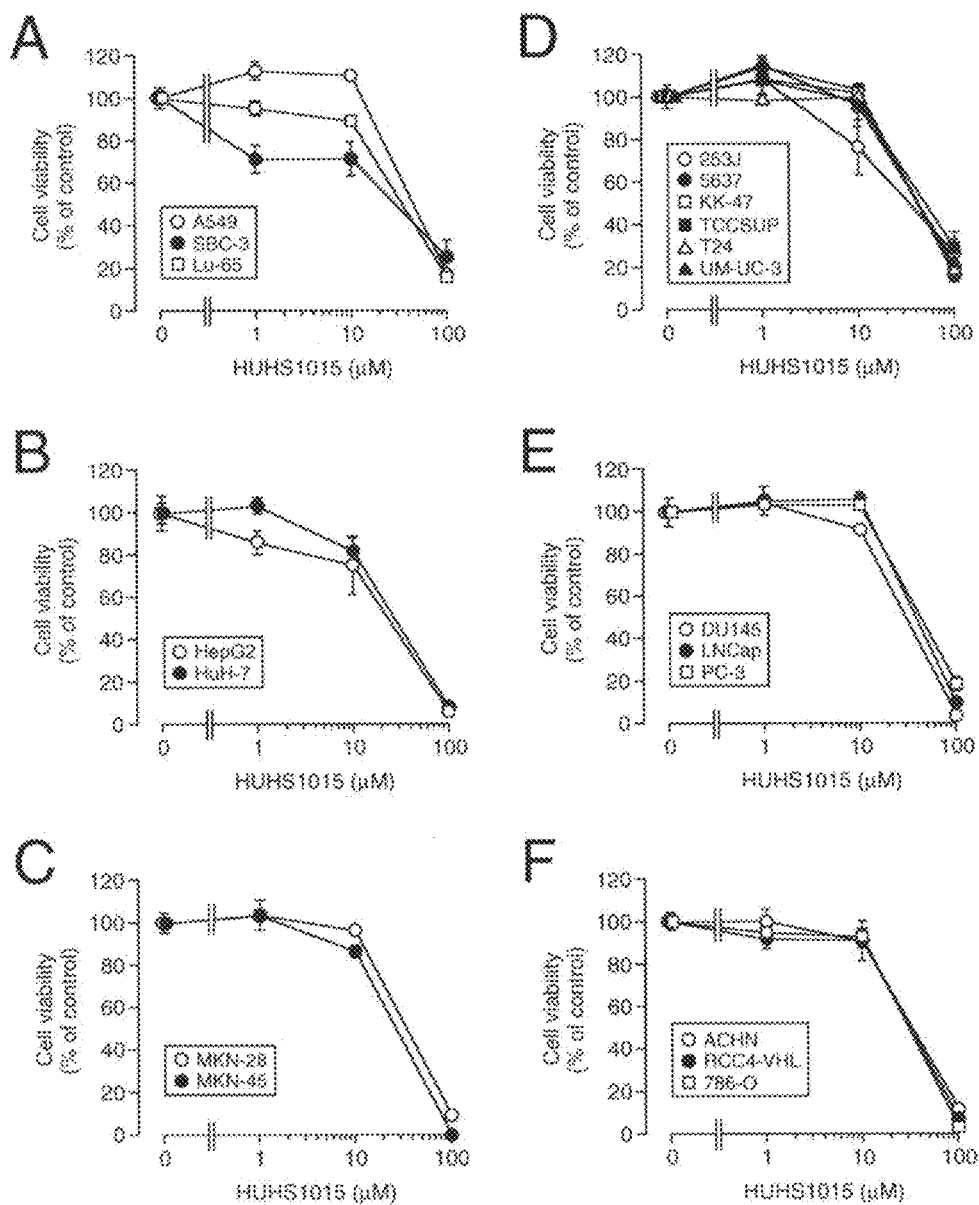
FIG. 3 shows an influence of HUHS1015 on the cell viability of various human cancer cells. The following cell lines treated or not treated with a given concentration of HUHS1015 for 24 hr were subjected to MTT assay. (A) lung cancer cell line (B) liver cancer cell line (C) gastric cancer cell line (D) bladder cancer cell line (E) prostate cancer cell line (F) kidney cancer cell line. In the graphs, each point shows the mean ($\pm$SEM) (n=4) of % control. As a control, MTT intensity of the cells not treated with HUHS1015 was used.
Figure 4:
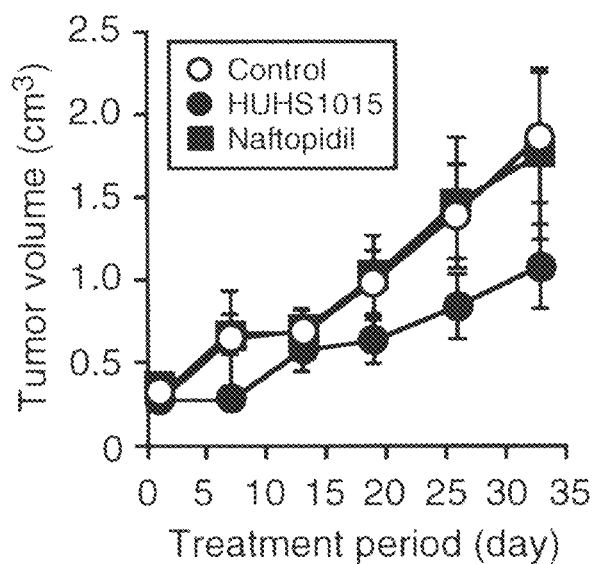
FIG. 4 shows an influence of HUHS1015 on the growth of gastric cancer cell line (MKN45). MKN45 gastric cancer cells were subcutaneously inoculated into the flank of mouse, and 1 week later (day 0), 25 μM of HUHS1015 and 25 μM of naftopidil were intraperitoneally administered (twice/1 week). As a control, a mouse administered with saline was used. The time-course changes (A) of the tumor volume (mean$\pm$SEM, n=7) and the results (B) of tumor weight (mean$\pm$SEM, n=7) after the lapse of 33 days are shown. P value, Dunnett's test. NS, not significant
Figure 4:
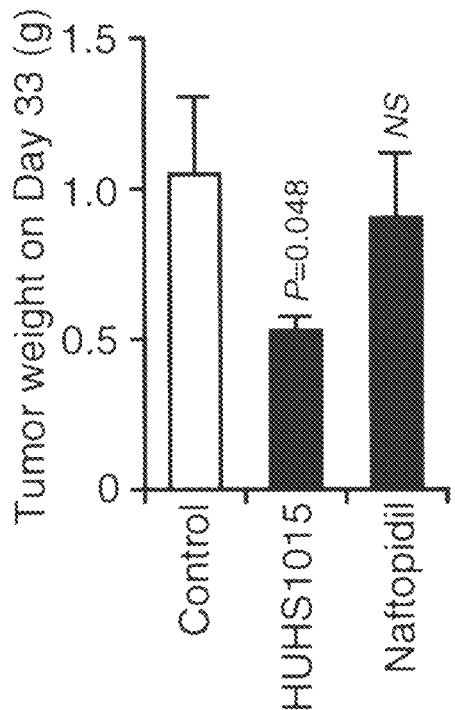

HUHS1015 could also reduced the cell viability in a concentration dependent manner at 1-100 μM even in cell lines other than the mesothelioma cell line:
human lung cancer cell lines (A549, SBC-3, and Lu-65 cells) (FIG. 3A)
human liver cancer cell lines (HepG2 and HuH-7 cells) (FIG. 3B)
human gastric cancer cell lines (MKN-28 and MKN-45 cells) (FIG. 3C)
human bladder cancer cell lines (253J, 5637, KK-47, TCCSUP, T24, and UM-UC-3 cells) (FIG. 3D)
human prostate cancer cell lines (DU145, LNCap, and PC-3 cells) (FIG. 3E)
and human kidney cancer cell lines (ACHN, RCC4-VHL, and 786-O cells) (FIG. 3F)

The results of this experiment show that naftopidil and a derivative thereof (aryloxy derivative (particularly HUHS1015)) have a superior anticancer action on malignant mesothelioma cells. In addition, HUHS1015 also showed beneficial effects not only on malignant mesothelioma cells but also lung cancer cells, liver cancer cells, gastric cancer cells, and urinary organ cancer cells such as bladder, prostate and kidney cells and the like. The mechanism of the anticancer action of naftopidil and a derivative thereof is not known well at present. Naftopidil functions as an inhibitor of $\alpha_{1A}$- and $\alpha_{1D}$-adrenoceptors (Jpn J Pharmacol 1999; 79:447-454), and $\alpha_1$-adrenoceptor is linked to $G_{q/11}$ protein to activate PKC (Biol Cell 2004; 96:343-348; Naunyn Schmiedebergs Arch Pharmacol 1997; 355:667-681; Eur J Pharmacol 1999; 375: 261-276). Therefore, the anticancer action of naftopidil was assumed to be ascribable to PKC inhibition related to $\alpha_1$-adrenoceptor blocking. However, such assumption is not correct since the apoptosis of malignant mesothelioma cells, which is induced by naftopidil, is not enhanced by a PKC inhibitor, GF109203X, and knock-down of $\alpha_1$-adrenoceptor promotes growth of malignant mesothelioma cells. That is, it is clear that the apoptosis action of naftopidil is independent of PKC and $\alpha_1$-adrenoceptor.

The aryloxy derivative, particularly HUHS1015, of the present invention shows a superior anticancer action, and further affords an important clue to the elucidation of the mechanism of the anticancer action of naftopidil (and a derivative thereof).

Experimental Example 2

Cancer Cell Proliferation Suppressive Action of Naftopidil Derivative (HUHS1015)

Nude BALB/c-nu/nu mouse (male, 6 week-old) was purchased from Japan SLC, Inc. (Shizuoka, Japan). MKN45 cells (1×10⁷ cells) were suspended in a culture medium (200 μl) containing Matrigel (BD Biosciences, San Jose, Calif., USA) and subcutaneously inoculated to the flank of the mouse under general anesthesia with pentobarbital. HUHS1015 (0.23 mg/mouse 25 μM) or naftopidil (0.25 mg/mouse 25 μM) was diluted with saline. At 1 week (Day 0) after inoculation, intraperitoneal administration of saline, HUHS1015 or naftopidil twice per week was started. The longitudinal length (L) and transverse length (S) of the inoculated tumor were measured with calipers, and the tumor volume (V) was calculated from the following formula:

$$V = L \times S^2 \times 1/2$$

The mouse was sacrificed on day 33, the tumor was isolated and the weight thereof was measured.

As a result, it was confirmed that the antitumor effect of HUHS1015 on gastric cancer was superior to naftopidil.

INDUSTRIAL APPLICABILITY

The aryloxy derivative provided by the present invention shows a cell proliferation suppressive action on a wide range of cancer cells.

The invention claimed is:

1. A method for treatment of cancer, wherein the cancer is at least one kind selected from the group consisting of mesothelioma, lung cancer, liver cancer, gastric cancer and bladder cancer, comprising administering an effective amount of a compound represented by the formula (I)

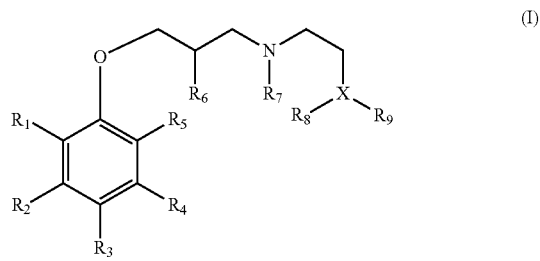

(I)

wherein
either $R^1$ and $R^2$ or $R^2$ and $R^3$ form a benzene ring together with a carbon atom bonded thereto;

$R^4$, $R^5$, and the remaining substituent of $R^1$ and $R^3$ that does not form a benzene ring with $R^2$ are the same or different and each is a hydrogen atom, a halogen atom or a $C_{2-6}$ alkenyl group;

$R^6$ is a hydrogen atom, a hydroxyl group or a $C_{1-6}$ alkoxy group;

$R^7$ and $R^8$ are the same or different and each is a hydrogen atom or a $C_{1-6}$ alkyl group;

X is N; and $R^9$ is an optionally substituted $C_{6-10}$ aryl group or an optionally substituted $C_{1-10}$ alkyl group, or a pharmaceutically acceptable salt thereof to a patient in need thereof.

2. The method according to claim 1, wherein the compound represented by the formula (I) is 1-((2-((2-methoxyphenyl)amino)ethyl)amino)-3-(1-naphthyloxy)propan-2-ol.

3. A compound represented by the formula (I)

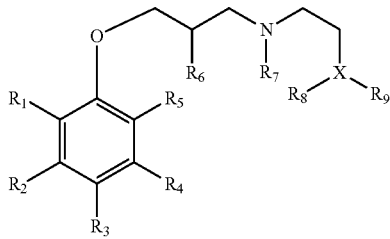

(I)

wherein either $R^1$ and $R^2$ or $R^2$ and $R^3$ form a benzene ring together with a carbon atom bonded thereto;

$R^4$, $R^5$, and the remaining substituent of $R^1$ and $R^3$ that does not form a benzene ring with $R^2$ are the same or different and each is a hydrogen atom, a halogen atom or a $C_{2-6}$ alkenyl group;

$R^6$ is a hydrogen atom, a hydroxyl group or a $C_{1-6}$ alkoxy group;

$R^7$ and $R^8$ are the same or different and each is a hydrogen atom or a $C_{1-6}$ alkyl group;

X is N; and $R^9$ is an optionally substituted $C_{6-10}$ aryl group or an optionally substituted $C_{1-10}$ alkyl group or a pharmaceutically acceptable salt thereof.

4. The compound according to claim 3, wherein the compound represented by the formula (I) is 1-((2-((2-methoxyphenyl)amino)ethyl)amino)-3-(1-naphthyloxy)propan-2-ol, or a pharmaceutically acceptable salt thereof.

5. The compound according to claim 3, wherein $R^1$ and $R^2$ form a benzene ring together with a carbon atom bonded thereto.

6. The compound according to claim 3, wherein $R^3$, $R^4$, and $R^5$ are each a hydrogen atom.

7. The compound according to claim 3, wherein $R^6$ is a hydroxyl group.

8. The compound according to claim 3, wherein $R^7$ is a hydrogen atom.

9. The compound according to claim 3, wherein $R^8$ is a hydrogen atom.

10. The compound according to claim 3, wherein $R^9$ is an optionally substituted phenyl group.

11. The method according to claim 1, wherein $R^1$ and $R^2$ form a benzene ring together with a carbon atom bonded thereto.

12. The method according to claim 1, wherein $R^3$, $R^4$, and $R^5$ are each a hydrogen atom.

13. The method according to claim 1, wherein $R^6$ is a hydroxyl group.

14. The method according to claim 1, wherein $R^7$ is a hydrogen atom.

15. The method according to claim 1, wherein $R^8$ is a hydrogen atom.

16. The method according to claim 1, wherein $R^9$ is an optionally substituted phenyl group.

* * * * *